(12) United States Patent
Masters

(10) Patent No.: US 10,016,534 B2
(45) Date of Patent: Jul. 10, 2018

(54) PROTEIN BIOMATERIAL AND BIOCOACERVATE VESSEL GRAFT SYSTEMS AND METHODS OF MAKING AND USING THEREOF

(75) Inventor: David B. Masters, Minneapolis, MN (US)

(73) Assignee: Gel-Del Technologies, Inc., St. Paul, MN (US)

( * ) Notice: Subject to any disclaimer, the term of this patent is extended or adjusted under 35 U.S.C. 154(b) by 984 days.

(21) Appl. No.: 13/131,083

(22) PCT Filed: Nov. 17, 2009

(86) PCT No.: PCT/US2009/064777
§ 371 (c)(1),
(2), (4) Date: Oct. 17, 2011

(87) PCT Pub. No.: WO2010/057177
PCT Pub. Date: May 20, 2010

(65) Prior Publication Data
US 2012/0041539 A1 Feb. 16, 2012

Related U.S. Application Data

(60) Provisional application No. 61/115,375, filed on Nov. 17, 2008.

(51) Int. Cl.
*A61F 2/82* (2013.01)
*A61L 31/16* (2006.01)
(Continued)

(52) U.S. Cl.
CPC ............ *A61L 31/16* (2013.01); *A61L 24/0015* (2013.01); *A61L 24/043* (2013.01); *A61L 24/108* (2013.01);
(Continued)

(58) Field of Classification Search
CPC .................................... A61F 2/06; A61F 2/82
(Continued)

(56) References Cited

U.S. PATENT DOCUMENTS

| 3,996,934 A | 12/1976 | Zaffaroni ....................... 424/434 |
| 4,060,081 A | 11/1977 | Yannas ....................... 623/15.12 |

(Continued)

FOREIGN PATENT DOCUMENTS

| CA | 1239755 | 8/1988 | ............... A61F 2/00 |
| CA | 1245527 | 11/1988 | ............ A61M 29/00 |

(Continued)

OTHER PUBLICATIONS

US 5,679,669, 10/1997, Colvard (withdrawn)
(Continued)

*Primary Examiner* — Matthew Schall
(74) *Attorney, Agent, or Firm* — Craige Thompson; Thompson Patent Law

(57) ABSTRACT

The present invention relates to protein biocoacervates and biomaterials vessel graft systems used in cardiovascular applications and other medical applications, the components utilized in the vessel graft systems and the methods of making and using such systems. More specifically the present invention relates to protein biocoacervates and biomaterials vessel graft systems used in various medical applications and/or the devices used in such vessel graft systems including, but not limited to, vessel grafts as drug delivery devices for the controlled release of pharmacologically active agents, tubular grafts, vascular grafts, protein biomaterial sutures and biomeshes, protein biomaterial adhesives and glues, and other biocompatible biocoacervate or biomaterial devices used in the vessel graft systems of the present invention.

17 Claims, 22 Drawing Sheets

(51) Int. Cl.

| | |
|---|---|
| *A61L 24/00* | (2006.01) |
| *A61L 24/04* | (2006.01) |
| *A61L 24/10* | (2006.01) |
| *A61L 27/26* | (2006.01) |
| *A61L 27/50* | (2006.01) |
| *A61L 27/54* | (2006.01) |
| *A61L 31/04* | (2006.01) |

(52) U.S. Cl.
CPC ............ *A61L 27/26* (2013.01); *A61L 27/507* (2013.01); *A61L 27/54* (2013.01); *A61L 31/041* (2013.01); *A61L 31/047* (2013.01); *A61L 2300/802* (2013.01)

(58) Field of Classification Search
USPC ....................................................... 623/1.13
See application file for complete search history.

(56) References Cited

U.S. PATENT DOCUMENTS

| | | | |
|---|---|---|---|
| 4,226,848 A | 10/1980 | Nagai | 514/772.1 |
| 4,250,163 A | 2/1981 | Nagai | 514/772.1 |
| 4,252,759 A | 2/1981 | Yannas | 264/86 |
| 4,280,954 A | 7/1981 | Yannas | 530/356 |
| 4,286,592 A | 9/1981 | Chandrasekaran | 424/448 |
| 4,292,299 A | 9/1981 | Suzuki | 424/435 |
| 4,347,234 A | 8/1982 | Wahlig | 424/426 |
| 4,350,629 A | 9/1982 | Yannas | 530/356 |
| 4,394,370 A | 7/1983 | Jefferies | 606/76 |
| 4,418,691 A | 12/1983 | Yannas | 424/548 |
| 4,438,253 A | 3/1984 | Casey et al. | 528/86 |
| 4,448,718 A | 5/1984 | Yannas | 530/356 |
| 4,458,678 A | 7/1984 | Yannas | 602/48 |
| 4,474,752 A | 10/1984 | Haslam | 424/78 |
| 4,505,266 A | 3/1985 | Yannas | 128/898 |
| 4,517,173 A | 5/1985 | Kizawa | 424/435 |
| 4,518,721 A | 5/1985 | Dhabhar | 523/120 |
| 4,522,753 A | 6/1985 | Yannas | 530/356 |
| 4,526,938 A | 7/1985 | Churchill et al. | 525/415 |
| 4,553,545 A | 11/1985 | Maass | 606/198 |
| 4,572,832 A | 2/1986 | Kigasawa | 514/772.1 |
| 4,600,533 A | 7/1986 | Chu | 530/356 |
| 4,652,441 A | 3/1987 | Okada et al. | 424/497 |
| 4,713,243 A | 12/1987 | Schiraldi | 424/676 |
| 4,733,665 A | 3/1988 | Palmaz | 606/108 |
| 4,739,762 A | 4/1988 | Palmaz | 623/1.11 |
| 4,780,450 A | 10/1988 | Sauk | 514/2 |
| 4,787,900 A | 11/1988 | Yannas | 600/36 |
| 4,800,882 A | 1/1989 | Gianturco | 606/194 |
| 4,801,299 A | 1/1989 | Brendel | 623/1 |
| 4,849,141 A | 7/1989 | Fujioka | 264/207 |
| 4,894,232 A | 1/1990 | Reul | 424/439 |
| 4,900,554 A | 2/1990 | Yanagibashi | 424/448 |
| 4,902,289 A | 2/1990 | Yannas | 623/1.47 |
| 4,907,336 A | 3/1990 | Gianturco | 29/515 |
| 4,915,948 A | 4/1990 | Gallopo | 424/435 |
| 4,917,161 A | 4/1990 | Townend | 131/352 |
| 4,947,840 A | 8/1990 | Yannas | 602/50 |
| 4,955,893 A | 9/1990 | Yannas | 606/154 |
| 4,959,217 A | 9/1990 | Sanders | 424/473 |
| 5,035,706 A | 7/1991 | Gianturco et al. | 606/198 |
| 5,037,392 A | 8/1991 | Hillstead | 606/194 |
| 5,041,126 A | 8/1991 | Gianturco | 623/1.15 |
| 5,041,292 A | 8/1991 | Feijen | 424/484 |
| 5,100,669 A | 3/1992 | Hyon et al. | 424/426 |
| 5,102,417 A | 4/1992 | Palmaz | 606/195 |
| 5,137,729 A | 8/1992 | Kuroya | 424/435 |
| 5,147,385 A | 9/1992 | Beck et al. | 128/898 |
| 5,188,837 A | 2/1993 | Domb | 424/450 |
| 5,192,802 A | 3/1993 | Rencher | 514/535 |
| 5,282,824 A | 2/1994 | Gianturco | 623/1.13 |
| 5,298,258 A | 3/1994 | Akemi | 424/484 |
| 5,314,915 A | 5/1994 | Rencher | 514/535 |
| 5,316,023 A | 5/1994 | Palmaz et al. | 128/898 |
| 5,324,775 A | 6/1994 | Ree | 525/54.2 |
| 5,330,768 A | 7/1994 | Park et al. | 424/501 |
| 5,423,739 A | 6/1995 | Phipps | 604/20 |
| 5,443,483 A | 8/1995 | Kirsch | 606/74 |
| 5,447,940 A | 9/1995 | Harvey | 514/310 |
| 5,489,304 A | 2/1996 | Orgill | 128/898 |
| 5,512,291 A | 4/1996 | Li | 424/443 |
| 5,573,934 A | 11/1996 | Hubbell | 435/177 |
| 5,591,224 A | 1/1997 | Schwartz | 613/1.22 |
| 5,607,445 A | 3/1997 | Summers | 623/1.22 |
| 5,642,749 A | 7/1997 | Perryman | 135/66 |
| 5,665,428 A | 9/1997 | Cha | 427/213.3 |
| 5,700,478 A | 9/1997 | Cha | 427/213 |
| 5,676,699 A | 10/1997 | Gogolewski | 623/16.11 |
| 5,709,683 A | 1/1998 | Bagby | 606/61 |
| 5,716,411 A | 2/1998 | Orgill | 435/371 |
| RE35,748 E | 3/1998 | Luck | 514/2 |
| 5,759,582 A | 6/1998 | Leong | 424/492 |
| 5,773,019 A | 6/1998 | Ashton | 424/423 |
| 5,783,214 A | 7/1998 | Royer | 424/499 |
| 5,834,232 A | 11/1998 | Bishop | 435/68.1 |
| 5,948,427 A | 9/1999 | Yamamoto | 424/426 |
| 5,981,568 A | 11/1999 | Kunz | 514/411 |
| 6,179,834 B1 | 1/2001 | Buysse | 606/41 |
| 6,210,429 B1 | 4/2001 | Vardi | 623/1.11 |
| 6,248,110 B1 | 6/2001 | Reiley | 606/93 |
| 6,287,765 B1 | 9/2001 | Cubicciotti | 435/6 |
| 6,291,582 B1 | 9/2001 | Dordick | 525/54.1 |
| 6,342,250 B1 | 1/2002 | Masters | 424/484 |
| 6,371,988 B1 | 4/2002 | Pafford | 623/17.11 |
| 2001/0008636 A1 | 7/2001 | Yamamoto | 424/426 |
| 2001/0020086 A1 | 9/2001 | Hubbell | 530/322 |
| 2002/0028243 A1 | 3/2002 | Masters | 424/484 |
| 2002/0052572 A1 | 5/2002 | Franco | 623/1.11 |
| 2002/0065553 A1 | 5/2002 | Weber | 606/1 |
| 2003/0028204 A1 | 2/2003 | Li | 606/152 |
| 2004/0002558 A1 | 1/2004 | McKay | 623/23 |
| 2006/0073207 A1 | 4/2006 | Masters et al. | |
| 2006/0210601 A1 | 9/2006 | Yunoki | 514/12 |
| 2008/0262596 A1 | 10/2008 | Xiao | |

FOREIGN PATENT DOCUMENTS

| | | | |
|---|---|---|---|
| CA | 2134997 | 11/1994 | ............ A61F 2/04 |
| CA | 2171047 | 3/1996 | ............ A61F 2/06 |
| CA | 2175722 | 5/1996 | ............ A61F 2/04 |
| CA | 2185740 | 9/1996 | ............ A61F 2/06 |
| CA | 2192520 | 12/1996 | ............ A61F 2/06 |
| EP | 0258780 A2 | 8/1987 | ............ C08G 63/66 |
| EP | 0 567 234 A1 | 3/1993 | ............ A61K 47/42 |
| EP | 0 636 378 B1 | 7/1994 | ............ A61L 31/00 |
| WO | WO 93/24150 | 12/1993 | ............ A61K 47/48 |
| WO | WO 97/32543 | 9/1997 | ............ A61F 2/06 |
| WO | WO 97/32544 | 9/1997 | ............ A61F 2/06 |
| WO | WO 97/41803 | 11/1997 | ............ A61F 2/06 |
| WO | WO 99/32613 A1 | 7/1999 | ............ C12N 9/98 |
| WO | WO 0183522 A2 | 11/2001 | ............ C07K 14/00 |
| WO | WO 0187267 A1 | 11/2001 | ............ A61K 9/10 |

OTHER PUBLICATIONS

International Preliminary Report on Patentability and Written Opinion for International Application No. PCT/US2009/064777, dated May 17, 2011, 6 pages.

AAPS: Annual Meeting & Exposition, *Symposia Abstracts & Biographies*, Boston, MA, Nov. 2, 1997, pp. 25-27.

Abbott, et al., *Vascular Grafts: Characteristics and Routine Selection of Prostheses*, Vascular Surgery, a Comprehensive Review, 5th Edition.

Abstracts, *Eighth International Symposium on Recent Advances in Drug Delivery Systems*, Feb. 24, 1997, Salt Lake City, UT, pp. 36-39, 138-140.

*American Red Cross Open to Partners for New Fibrin Sealant*, Genetic Engineering News, Mar. 1995, p. 30.

Anderson, *Characterization of Silk-like Proteins and Processing for Biomedical Applications*, Protein-Based Materials, 1997, pp. 371-423.

(56) References Cited

OTHER PUBLICATIONS

Cappello, et al., *Genetic Engineering of Structural Protein Polymers*, Biotechnology Progress, 1990, pp. 198-202.
Cappello, et al., *Microbial Production of Structural Polymers*, (ed. Mobley), 1994 Carl Hanser Verlag, Munich, pp. 35-92.
Cappello, *Protein Engineering for Biomaterials Applications*, Current Opinion in Structural Biology, 1992, 2:582-586.
Caruana, *New Drugs Spur Novel Delivery Systems*, Chemical Engineering Progress, Jul. 1997, pp. 15-19.
Choi, et al. Implantation Biology: The Host Response and Biomedical Devices. *The Effect of Biomaterials on the Host*, CRC Press, Boca Raton 405 pages, 1994. Chapter 3, pp. 39-53.
Chvapil, et al., *Some Chemical and Biological Characteristics of a New Collagen-Polymer\* Compound Material*, J. Biomed. Mater. Res. vol. 3, pp. 315-331 (1969).
Davis, et al., *Chemically Cross-Linked Albumin Microspheres for the Controlled Release of Incorporated Rose Bengal After Instramuscular Injection Into Rabbits*, Journal of Controlled Release, 4 (1987) 293-302.
Dickinson, et al., *Biodegradation of a poly($\alpha$-amino acid) hydrogel. I. In vivo*, Journal of Biomedical Materials Research, vol. 15, 577-589 (1981).
Drug Delivery Systems (Program), Feb. 1998, San Francisco.
Dunn, et al., *Biomaterials Used in Orthopaedic Surgery*, Implantation Biology, CRC Press, Boca Raton, 1994, pp. 229-252.
Dutton, *Tissue Engineering: Continued Growth Expected as New Techniques Evolve*, Genetic Engineering News, Apr. 1998, pp. 21, 37.
Fernandes, et al., *Regulation of Polymeric Implants for Site-specific Drug Delivery*, Polymeric Site-specific Pharmcotherapy, Chapter 16, 1994, pp. 424-441.
Ghandehari, et al., *Genetic Engineering of Protein-Based Polymers: Potential in Controlled Drug Delivery*, Pharmaceutical Research, vol. 15, No. 6, 1998, pp. 813-815.
*Handbook of Food Science, Technology and Engineering*. Yiu, Hu H. (editor), 2006, CRC Press.
Harvey, *Utilizing Prostheses for Drug Delivery*, Implantation Biology, CRC Press, Boca Raton, 1994, pp. 329-345.
Heller, et al., *Controlled release of water-soluble macromolecules from Bioerodible Hydrogels*, Biomaterials 1983, vol. 4 October, pp. 262-266.
Http://www.merriam-webster.com/dictionary/binding (accessed Jan. 24, 2009).
Kelly, *Researchers Advancing Biopolymer Systems as Vehicles for Delivering Drugs*, Genetic Engineering News, May 15, 1997, pp. 1, 25, 32, 35, 36, 41.
Langer, *1994 Whitaker Lecture: Polymers for Drug Delivery and Tissue Engineering*, Annals of Biomedical Engineering, 1995, vol. 23, pp. 101-111.
Lewis, *New Directions in Research on Blood Substitutes*, Genetic Engineering News, Jun. 15, 1997, pp. 1, 10, 12, 20, 26, 33, 35, 36, 41.
Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.

Masters, Course Syllabus for Mayo Graduate Course, *Polymeric Site-Specific Drug Delivery*, Apr. 1998.
Masters, *Drug Delivery to Peripheral Nerves*, Polymeric Site-Specific Pharmacotherapy, 1994, pp. 443-455.
Masters, et al., *Liposphere Local Anesthetic Timed-Release for Perineural Site Application*, Pharmaceutical Research, vol. 15, No. 7, 1998, pp. 1038-1045.
Masters, et al., *Prolonged Regional Nerve Blockade by Controlled Release of Local Anesthetic from a Biodegradable Polymer Matrix*, Anesthesiology, vol. 79, No. 2, 1993, pp. 340-346.
Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.
Morrione; "The Formation of Collagen Fibers by the Action of Heparin on Soluble Collagen: An Electron Microscope Study"; 1952; J. Exp. Med.; 96(2): 107-14.
Morrow, *Companies to Take Broad Range of Approaches to Develop Rheumatoid Arthritis Therapies*, Genetic Engineering News, Jan. 15, 1997, pp. 1, 7, 9, 24.
Nomura, et al.; "Preparation and Some Properties of Type I Collagen from Fish Scales"; 1996; Biosci. Biotech. Biochem.; 60(12): 2092-2094.
Ohtani, *Three-Dimensional Organization of the Collagen Fibrillar Framework of the Human and Rat Livers*, Arch. Hist. Cytol., vol. 51, No. 5, 1988, pp. 473-788.
Peppas, et al. *New Challenges in Biomaterials*, Science, Mar. 1994, vol. 263, pp. 1715-1720.
Polymeric Materials Encyclopedia. Salamone, J.C. (editor), 1996, CRC Press. (see p. 7451).
Pramik, *Drug Delivery Firms Focus on Controlled Release Techniques*, Genetic Engineering News, Oct. 1, 1996, pp. 1, 38, 40.
Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.
Protein Polymer Technologies: 1994 Annual Report, *BioEngineered Tissue Repair and Regeneration*.
R&D, A Cahners Publication, *BioDerived Materials*, Jun. 1990, p. 58.
Ranade, *Drug Delivery Systems: 3A. Role of Polymers in Drug Delivery*, J.Clin. Pharmacol 1990; 30: 10-23.
Ranade, *Drug Delivery Systems: 3A. Role of Polymers in Drug Delivery*, J.Clin. Pharmacol 1990; 30: 107-120.
Ratner, et al., *An Introduction to Materials in Medicine*, Biomaterials Science, 1996.
Sedlak, *Hyal Pharmaceutical Looks for Home Run with HIT Drug Delivery System*, Genetic Engineering News, Sep. 1, 1995, p. 16.
Sedlak, *Signal Transduction Companies Moving Some Products to the Clinical Testing Environment*, Genetic Engineering News, Mar. 15, 1997, vol. 17, No. 6, pp. 1, 27, 36.
Skarda, et al., *Biodegradable Hydrogel for Controlled Release of Biologically Active Macromolecules*, Journal of Bioactive and Compatible Polymers, vol. 8, Jan. 1993, pp. 24-40.
*The Biological Production of Protein Polymers and Their Use*, Trends in Biotechnology, Nov. 1990, vol. 8, No. 11.
*Tissue Engineering*, Genetic Engineering News, Jan. 1998, pp. 33.
Urry, et al., *Protein-Based Materials with a Profound Range of Properties and Applications: The Elastin $\Delta T_t$Hydrophobic Paradigm*, Protein-Based Materials, 1997, pp. 133-177.

Cell culture studies reveal anti-proliferative activity of rapamycin (Fig 15). In the porcine model used, healing and hyperplasia from smooth muscle cells are linked at anastomosis site. (Fig 16).

Color Doppler (Fig 17) and CT-Scan (Fig 18) show open VasoGraft/femoral artery at 200 & 90-days, respectively.

PROTEIN BIOMATERIAL AND BIOCOACERVATE VESSEL GRAFT SYSTEMS AND METHODS OF MAKING AND USING THEREOF

RELATED APPLICATIONS

This application is a 35 U.S.C. 371 national stage filing from International Application No. PCT/US2009/064777 filed Nov. 17, 2009 and claims priority to U.S. Provisional Patent Application No. 61/115,375 filed Nov. 17, 2008, the teachings of which are incorporated herein by reference.

FIELD OF THE INVENTION

The present invention relates to protein biocoacervates and biomaterials vessel graft systems used in cardiovascular applications and other medical applications, the components utilized in the vessel graft systems and the methods of making and using such systems. More specifically the present invention relates to protein biocoacervates and biomaterials vessel graft systems used in various medical applications and/or the devices used in such vessel graft systems including, but not limited to, vessel grafts as drug delivery devices for the controlled release of pharmacologically active agents, tubular grafts, vascular grafts, protein biomaterial sutures and biomeshes, protein biomaterial adhesives and glues, and other biocompatible biocoacervate or biomaterial devices used in the vessel graft systems of the present invention.

SUMMARY OF THE INVENTION

The present invention relates to protein biocoacervate and/or biomaterial vessel graft systems used in cardiovascular applications and other medical applications and the components utilized in such vessel graft systems and the methods of making and using such systems. More specifically the present invention relates to protein biocoacervates and biomaterials vessel graft systems used in various medical applications and/or the devices/components used in such vessel graft systems including, but not limited to, 1) one or more vessel grafts including pharmacologically active agents (drugs) for the controlled release of pharmacologically active agents or one or more tubular grafts without such active agents, 2) one or more protein biomaterial sutures and/or threads, and/or 3) one or more protein biomaterial adhesives and/or glues.

Generally, the protein biocoacervates, related biomaterials and vessel graft devices derived from these biocoacervates or related biomaterials include an amorphous material comprising one or more biocompatible primary proteins, one or more glycosaminoglycans and one or more biocompatible solvents. It is noted that the term glycosaminoglycan may also be considered to include mucopolysaccharides and proteoglycans. Additionally, the biocoacervates and biomaterials may also include one or more secondary proteins, one or more pharmacologically active agents and/or one or more additive materials to provide a therapeutic entity or enhance the chemical and/or mechanical properties of the biocoacervate or biomaterial. A description of the biocoacervates and biomaterials that may be used with the vessel graft systems and components of the present invention is found in U.S. patent application Ser. No. 10/929,117, the entire contents of which are incorporated by reference herein.

The present invention also relates to a method of making a vessel graft system, including the process for manufacturing the tubular component of the system and the one or more fastening device(s), such as sutures, meshes, bioglues or adhesives and the like, one or more of which include a protein biocoacervate and/or biomaterial. The method of preparation of the biocoacervate and biomaterials used to make the vessel grafts and fasteners included in the vessel graft system of the present invention includes first forming a biocompatible coacervate including one or more biocompatible primary proteins, one or more glycosaminoglycans and one or more biocompatible solvents. In various embodiments, the biocoacervate is formed by also including one or more secondary proteins. The biocoacervate is generally assembled by combining one or more primary proteins such as collagen, fibrin or fibronectin and one or more glycosaminoglycans such as heparin, chondroiten sulfate or heparin sulfate to a heated and optionally stirred solution of one or more biocompatible solvents such as water, DMSO, or ethanol. One or more secondary proteins such as elastin or albumen may also be added to the primary protein/glycosaminoglycan solution. Upon adding the glycosaminoglycan to the heated solution containing the primary protein(s), and in various embodiments the secondary protein, an amorphous body falls out. The amorphous protein body generally falls out of the solution as an amorphous precipitate material allowing it to be easily extracted from the solution. Generally, the precipitant of the present invention falls out of solution due to a chemical and/or physical change thereby forming the water insoluble amorphous biocoacervate. Once extracted from the solution, the amorphous material is allowed to cool thereby forming a cohesive elastic coacervate. It is noted that the material has elastic mechanical properties similar to the material utilized in rubberbands and is capable of being melted and formed into any type shape or configuration, thereby demonstrating thermoplastic characteristics. The biocoacervate is generally stable in water. However, the biocoacervate dissolves when placed in saline solution. A biomaterial that does not dissolve in saline solution may be produced from the biocoacervate by setting the biocoacervate utilizing a crosslinking agent, such as gluteraldehyde, utilizing a crosslinking technique like dehydrothermal processes, such as heat radiation, and/or by utilizing any crosslinking means that cause the proteins and/or glycosaminoglycans to crosslink.

As previously mentioned, the biocoacervate or biomaterial may also optionally include additional polymeric materials and/or therapeutic entities, such as one or more phatinacologically active agents, that would provide additional beneficial characteristics or features to the coacervate. Generally, these materials and/or entities may be added to the solution during the formation of the coacervate. Alternatively, these materials and/or entities may be added after the coacervate has been formed utilizing any means to disperse the agent(s) within the biocoacervate such as adding and/or dissolving the agent(s) into the melted form of the coacervate or allowing diffusion and/or loading the agent(s) into the unmelted coacervate.

The above described process has many advantages if one or more pharmacologically active agents are incorporated into the biocoacervate. For example, the controlled release characteristics of the biocoacervates and biomaterials of the present invention provide for a higher amount of pharmacologically active agent(s) that may be incorporated into the biocoacervate or biomaterial. Additionally, the pharmacologically active agent(s) may be substantially homogeneously distributed throughout biocoacervate, biomaterial or corresponding devices. This homogenous distribution provides for a more systematic and consistent release of the pharmacologically active agent(s). As a result, the release characteristics of the pharmacologically active agent from the biocoacervate, biomaterial and/or device are enhanced.

Inasmuch as the biocoacervates, biomaterials and corresponding vessel graft devices of embodiments of the present invention provide the sustained release of one or more pharmacologically active agents in a rate controllable fashion, they are also capable of delivering other migration-vulnerable and/or reactive drug delivery devices and furthermore are produced in a manner that reduces, if not eliminates, the risk of residual solvent toxicity or adverse tissue reaction. Also, the biocoacervates, biomaterials and corresponding vessel graft devices of the present invention provide a method of effecting a local therapeutic response in a patient in need of such treatment. Specifically, embodiments of the vessel graft systems of the present invention may be administered to prompt a desired therapeutic response that may be local and/or systemic. In various embodiments, the therapeutic response effected is an analgesic response, an anti-inflammatory response, an anesthetic response, a response preventative of an immunogenic response, an anti-coagulatory response, a cell anti-proliferation response, a genetic response, an antimitotic response, a protein assembly response, an antibacterial response, a vaccination response, combinations of these, and the like. As used herein, unless stated otherwise, all percentages are percentages based upon the total mass of the composition being described, e.g., 100% is total.

The foregoing and additional advantages and characterizing features of the present invention will become increasingly apparent to those of ordinary skill in the art by references to the following detailed description and to the drawings.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein.

BRIEF DESCRIPTION OF THE CASE STUDY FIGURES

Figure 7:
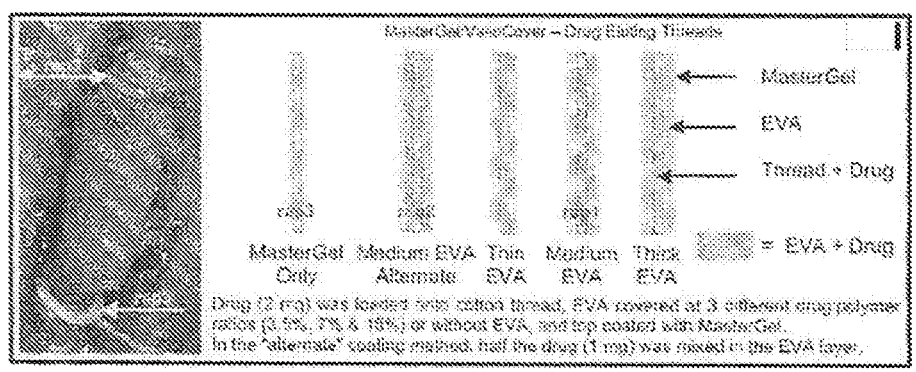
Figures 8, 9, 10, 11:
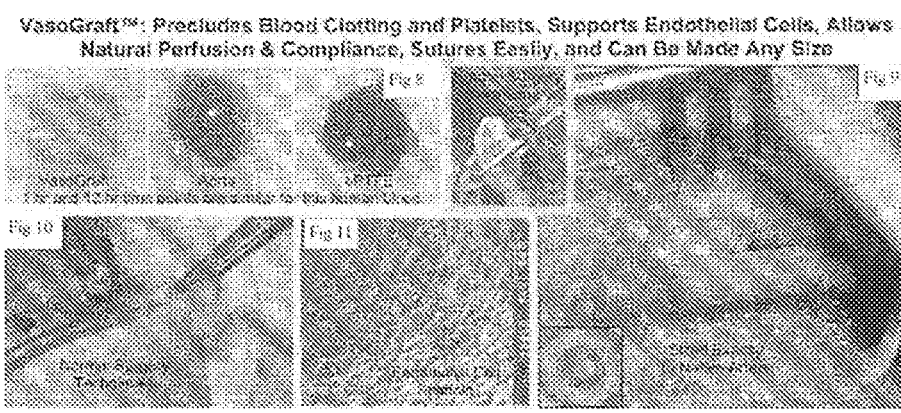
Figures 12, 13:
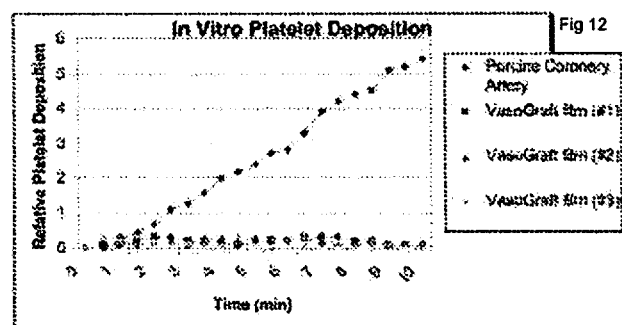
Figure 14:
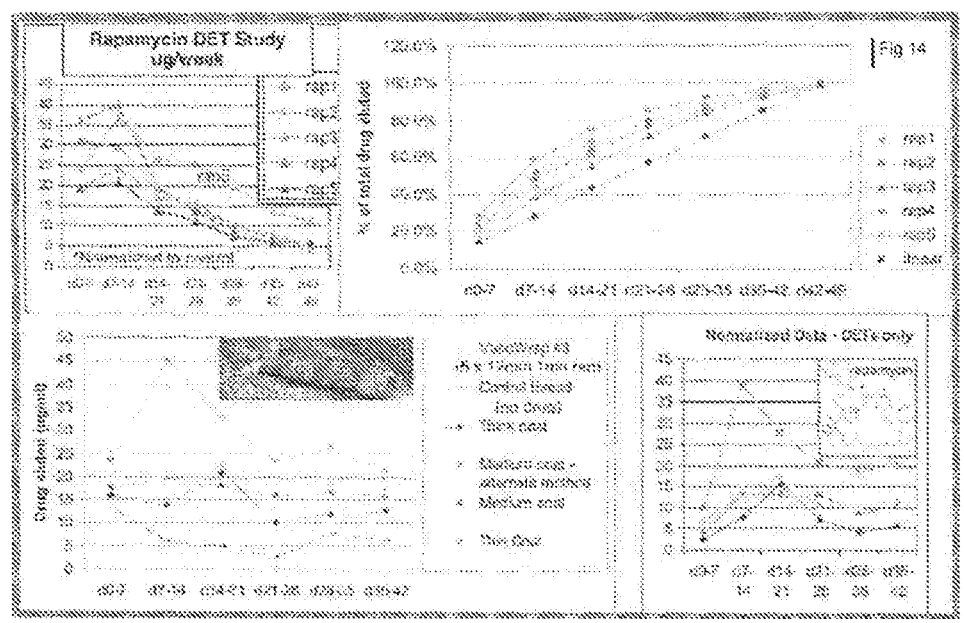
Figure 15:
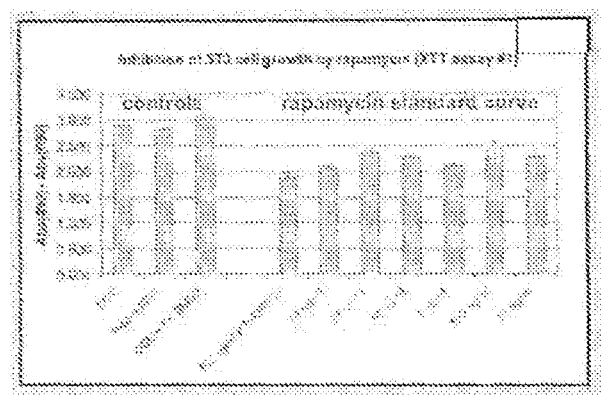
Figure 16:
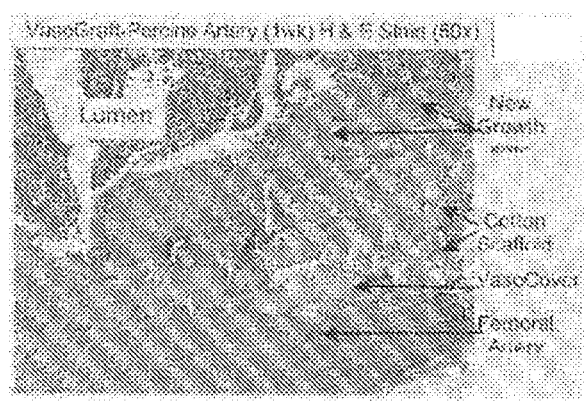
Figure 20:
Figure 21:
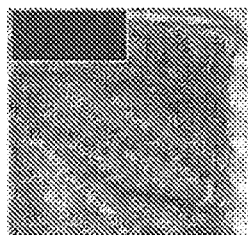
Figure 22:
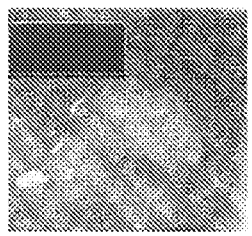
Figure 23:
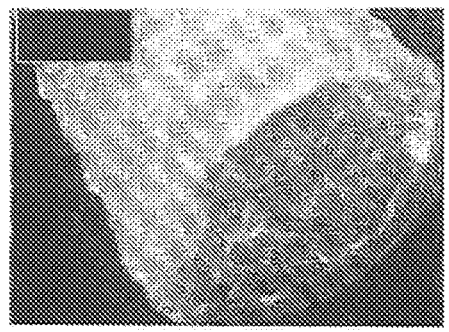
Figure 24:
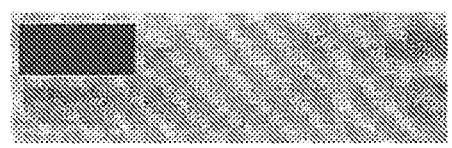
Figure 25:
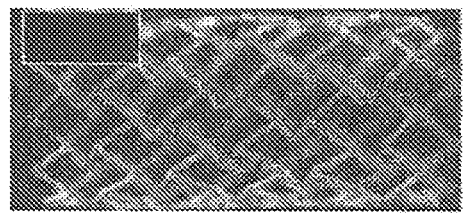
Figure 26:
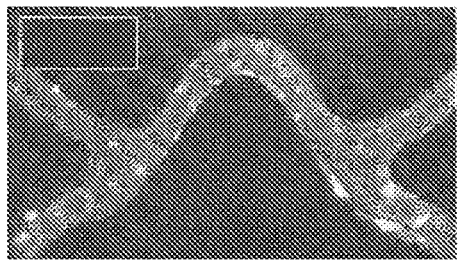

FIG. 7 depicts one embodiment of drug-eluting threads (DETs) using cotton thread evenly coated with drug into cotton or ethyl vinyl acetate (EVA);

FIG. 8 depicts surface blood contact and platelet studies of an embodiment of the present invention;

FIG. 9 depicts one embodiment of the DETs that provide targeted and slow release of drug over months to preclude smooth muscle cell hyperplasia, allowing the native artery to heal without clogging itself (i.e., stenosis) so that the artery and graft stay patent;

FIG. 10 depict another embodiment of a vessel of the present invention wherein standard surgical techniques were used with only post-op aspirin;

FIG. 11 depicts an embodiment of the vessel graft wherein endothelial cell attachment to the graft was accomplished with human umbilical vein endothelial cells (HUVEC cell line) pipeted into lumen of graft and incubated 4 days;

FIG. 12 depicts a graft illustrating surface blood contact and platelet studies;

FIG. 13 depicts a graft illustrating strength and perfusion studies;

FIG. 14 depicts elusion studies including EVA top coated with MasterGel/VasoCover, which provides predictable release kinetics, in vitro;

FIG. 15 depicts in vitro cell effects tested for rapamycin standard curve doses;

FIG. 16, 17, 18 and 19 depicts images and data related to DET-rapamycin application that prolongs or precludes smooth muscle cell hyperplasia in small diameter grafts, depending on proper delivery of drug dose at the anastomosis site;

FIG. 20 depicts MasterGlue, VasoCover, and VasoGraft that are made from MasterGel using GMP-ready scalable manufacturing that has already demonstrated long shelf life;

FIGS. 21 and 22 depicts an embodiment of MasterGlue™, MasterGlue is used as a sealant, tissue filler, and drug-elution vehicle to facilitate healing at anastomosis sites for injured or diseased vessels;

FIGS. 23, 24, 25 and 26 depict and embodiment of MasterGel that can be used to coat current vascular grafts or STENTS made from a variety of materials (e.g., ePTFE, poly urethane, cotton, steel, nitinol) at any coating thickness.

DETAILED DESCRIPTION OF THE INVENTION

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention.

The vessel graft systems and one or more of the components present in such systems of the present invention comprise one or more biocoacervates and/or biomaterials that are derived from one or more amorphous biocoacervate material(s) that generally include one or more primary proteins, one or more glycosaminoglycans and one or more biocompatible solvents. The amorphous biocoacervate material(s) of the present invention tend to have no real or apparent crystalline or fibrous form that can be seen by the naked eye or by light microscope at 400× or less. Such materials are different from other protein and glycosaminoglycan materials, which tend to be crystalline, fibrous or appears similar to balls of yarn. Also the biocoacervate and a number of the biomaterial embodiments of the present invention tend to have thermoplastic and viscoelastic properties. In various embodiments of the present invention the biocoacervates, biomaterials and devices may also include one or more secondary proteins.

Figure 1:
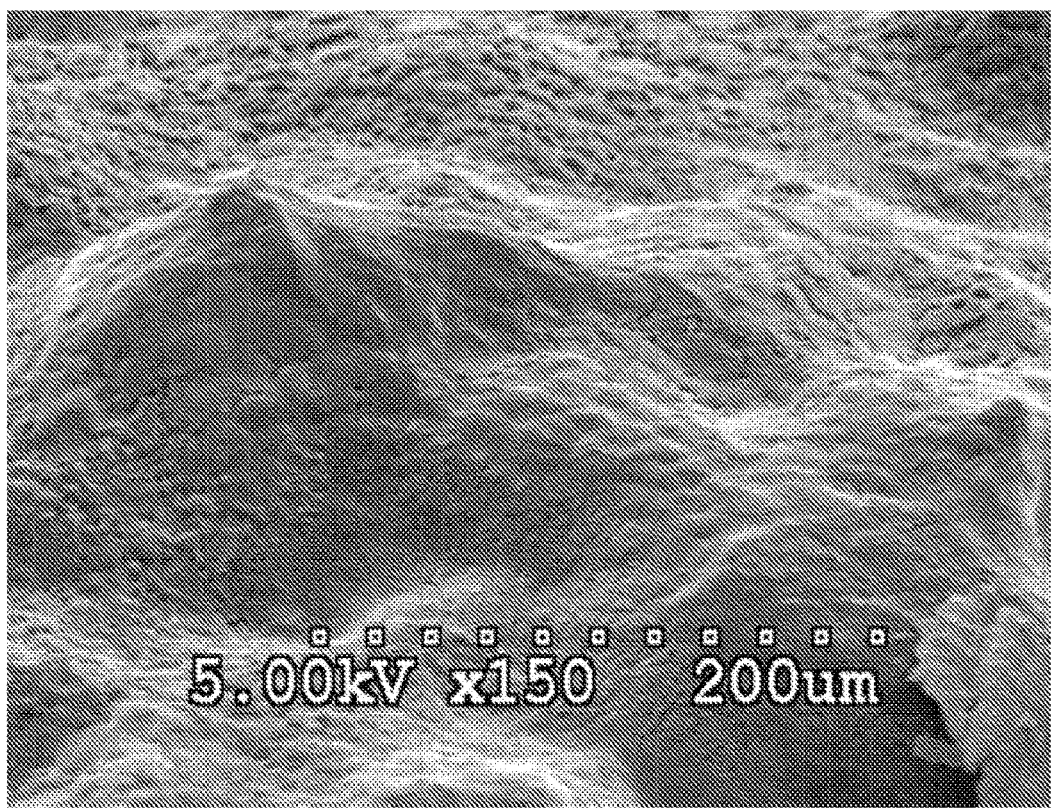
FIG. 1 depicts a magnified view of an embodiment of the biomaterial of the present invention illustrating the aggregated proteoids.
Figure 2A:
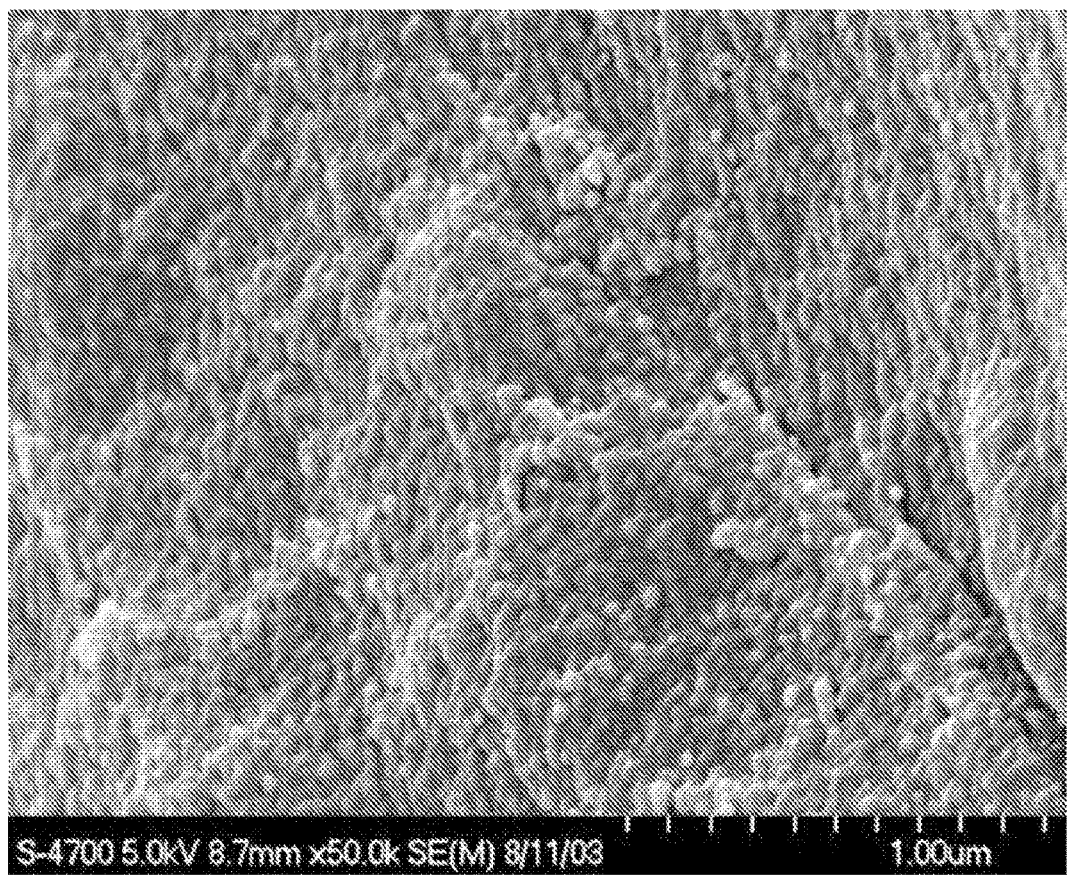
FIG. 2A, 2B, and 2C depicts a magnified view of an embodiment of the biomaterial of the present invention illustrating the aggregated proteoids.
Figure 2B:
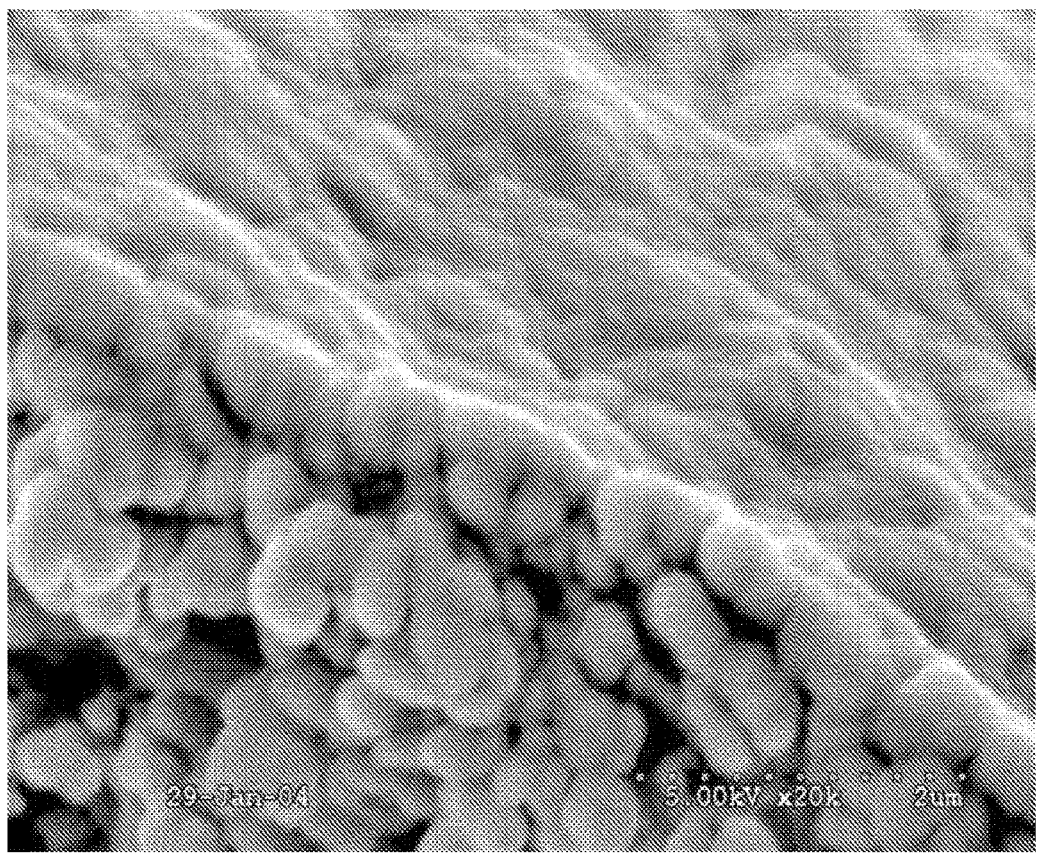
Figure 2C:
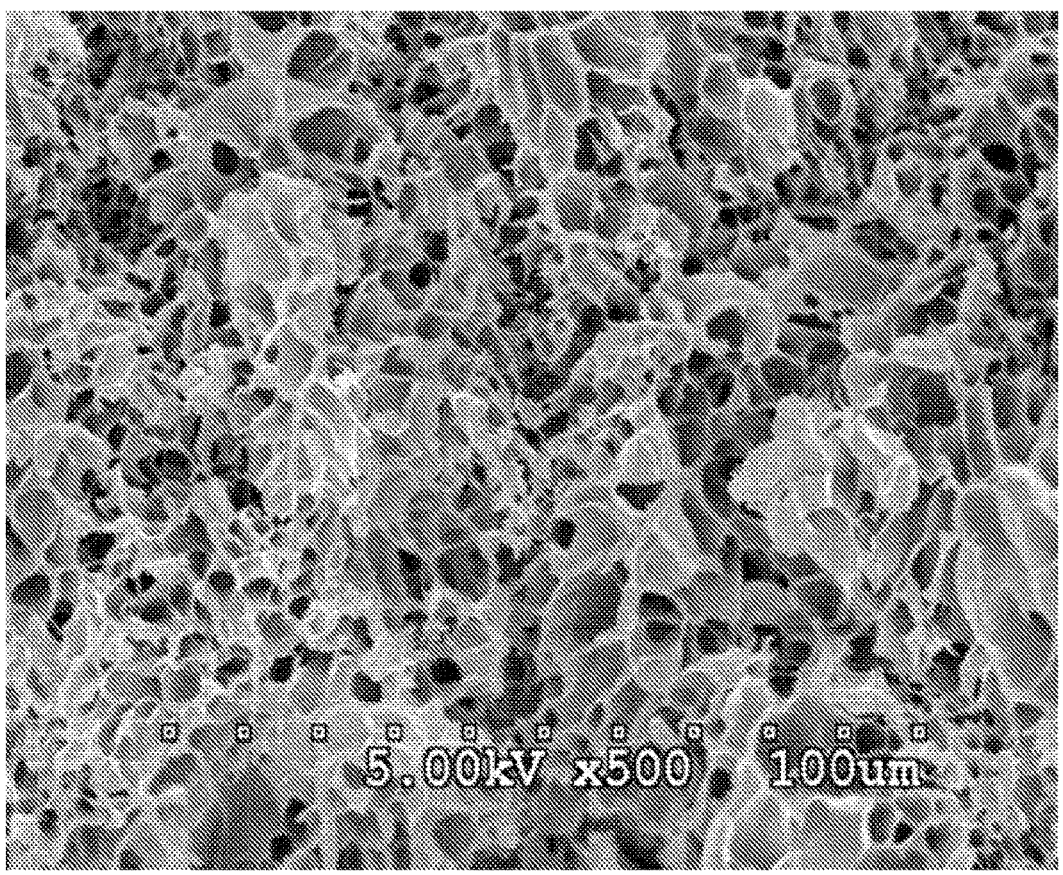

FIGS. 1 and 2a-b depict a magnified view of embodiments of the biomaterials of the present invention. As depicted in these figures, various embodiments of the biocoacervate of the present invention include a plurality of individual spherical complexes (hereinafter referred to as "proteoids"), which interact and aggregate with each other to form the biocoacervate. Generally, the proteoids found in the present invention are small microspheres comprising at least a primary protein, a glycosaminoglycan and a biocompatible solvent. The proteoids will tend to aggregate together to form the amorphous biocoacervate embodiments of the present invention. Also, it has been found that under certain conditions the proteoids can undergo strong intermolecular bonding that may alter their shape. FIG. 2c depicts an embodiment of the biocoacervate that has been crosslinked and freeze fractured to illustrate that the proteoids of this embodiment include inner cavities and crosslinks that hold the proteoids together into a single mass. These proteoids or spherical complexes generally range from 0.001 to 100 microns in size, in various embodiments 0.1 to 10 microns, but may vary in size depending upon the amount of swelling they experience. The swelling of biocoacervates including the proteoids may be controlled by crosslinking, pH, compression, salt content, solvent content (e.g. water or alcohol content) and/or temperature. Furthermore, the amount of swelling may be controlled by adjusting the various degrees of crosslinking of the biocoacervate before exposing the material to one or more solutions.

Additionally, embodiments of the biocoacervates, biomaterials and vessel graft devices of the present invention may also include one or more therapeutic pharmacologically active agents and/or one or more additive materials, such as structural or polymeric materials. It is noted that additional additive materials, such as humectants, biocompatible polymers (e.g. proteins, polyanhydride, polylactic acid, polyurethane and the like) and/or therapeutic entities, such as stents and other medical devices may be included in the material to provide various beneficial features such as mucoadhesion, strength, elasticity, structure, enhanced biocompatibility, enhanced drug delivery and drug absorption, therapeutic functions or any other desirable characteristics. In various embodiments of the present invention, the biocoacervates or biomaterials possess a relatively homogeneous distribution of the components, including a homogenous distribution of any pharmacologically active agents and additive materials.

The biocoacervates, biomaterials and the vessel graft systems and its components of the present invention are designed to retain the protein's natural activity and possess the capability of being formed into various sizes and configurations with structural integrity. Embodiments of the biocoacervates, biomaterials and the related devices are further designed to mimic the architectural framework of the body to support natural tissue growth. In various embodiments of the present invention the biocoacervates, biomaterials and the related vessel graft system and its components of the present invention are biointegratable thereby allowing the integration and remodeling of the material by the host tissue.

As previously mentioned, the biocoacervates, biomaterials and the related vessel graft system components normally comprise one or more biocompatible primary proteins and, in various embodiments, one or more secondary proteins. The primary and secondary proteins are generally soluble or are solubilized. Primary proteins normally have an affinity to bind with glycosaminoglycans and in some instances other proteins thereby indicating that functional groups are present on the primary proteins that attract and retain the glycosaminoglycans and possibly other proteins. Additionally, primary proteins when mixed with glycosaminoglycans in solution under proper conditions will generally form a precipitate that falls out of solution, whereas the secondary proteins will not form such a precipitate when placed in solution with glycosaminoglycans. Additionally, secondary proteins generally have a more limited binding affinity with glycosaminoglycans than their primary protein counterparts, but are attracted and retained by the primary proteins in the presence of glycosaminoglycans. However, secondary proteins have been found to add very beneficial characteristics to the biocoacervates of the present invention, such as elasticity, strength, biodurability, biocompatibility and the like. Generally, the amount of primary protein found in embodiments of the biocoacervate or biomaterials of the present invention may vary between from about 10% to about 90%, in various embodiments from about 20% to 80% by weight, and in some embodiments from about 50% to 70% by weight based upon the weight of the final biocoacervate or biomaterial. Alternatively, when present in the biocoacervate or biomaterials, the amount of secondary protein may vary between from about 1% to about 40%, in various embodiments from about 10% to 30% by weight, and most in some embodiments from about 15% to 25% by weight based upon the weight of the final biocoacervate or biomaterial.

The primary and secondary proteins utilized in the present invention may be synthetic proteins, genetically-engineered proteins, natural proteins or any combination thereof. In many embodiments of the present invention, the biocoacervates, biomaterials and the related vessel graft systems and its components include water-absorbing, biocompatible primary and secondary proteins. The utilization of a water-absorbing biocompatible protein included in the biocoacervate or biomaterial provides the advantage that, not only will the biocoacervates or biomaterials be bioresorbable, but may remodel to mimic and support the tissue it contacts. That is, the metabolites of any degradation and/or resorption of the water-absorbing biocompatible protein may be reused by the patient's body rather than excreted.

Additionally, the primary and secondary proteins of the present invention are generally purified and in a free-form state. Normally, free-form proteins are comprised of protein molecules that are not substantially crosslinked to other protein molecules, unlike tissues (e.g. decellularized tissue) or gelatins. Normally, tissue or gelatin is already in a crosslinked matrix form and is thereby limited in forming new intermolecular or intramolecular bonds. Therefore, the free-form protein molecules when added to solvent have the capacity to freely associate or intermingle with each other and other molecules or particles, such as solvents, pharmacologically active agents, additives and other proteins to form a homogeneous structure. Additionally, the binding sites of the free-form primary proteins for the attraction and retention of glycosaminoglycans or secondary proteins are generally available for binding whereas proteins derived from tissues and gelatins have generally lost some or most of its binding or interaction capability.

As previously suggested, the primary and secondary proteins utilized may either be naturally occurring, synthetic or genetically engineered. Naturally occurring primary proteins that may be utilized in biocoacervates, biomaterials and the vessel graft systems and its components of the present invention include, but are not limited to the following and their derivatives: collagen, bone morphogenic protein and its isoforms that contain glucosaminoglycan binding sites, albumin, interleukins, epidermal growth factors, fibronectin, laminin, thrombin, aprotinin, antithrombin III and any other biocompatible natural protein that includes glucosaminoglycan binding sites. Naturally occurring secondary proteins that may be utilized in biocoacervates, biomaterials and the vessel graft systems and its components of the present invention include, but are not limited to the following and their derivatives: fibrin, fibrinogen, elastin, albumin, ovalbumin, keratin, silk, silk fibroin, actin, myosin, thrombin, aprotinin, antithrombin III and any other biocompatible natural protein that have an affinity to primary proteins in the presence of glucosaminoglycans. Examples of primary and secondary proteins that are commercially available and may be utilized in some embodiments of the present invention include Type I soluble or insoluble collagen, insoluble or soluble elastin, and soluble albumen manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. It is noted that in various embodiments of the present invention, the insoluble proteins listed above would be processed to a soluble form prior to or during synthesis of a biocoacervate or biomaterial. It is further noted that combinations of natural proteins may be utilized to optimize desirable characteristics of the resulting biocoacervates and biomaterials, such as strength, degradability, resorption, etc. Inasmuch as heterogeneity in molecular weight, sequence and stereochemistry can influence the function of a protein in a biocoacervate or biomaterial, in some embodiments of the present invention synthetic or genetically engineered proteins are preferred in that a higher degree of control can be exercised over these parameters.

As previously suggested the primary and secondary proteins of the present invention are generally purified proteins. The purity of each natural protein component mixed in the solution phase (the process of making the coacervates and biomaterials will be described further below) during production of the coacervate include 20% or less other proteins or impurities, preferably 10% or less other proteins or impurities, more preferably 3% or less other proteins or impurities and if available ideally 1% or less other proteins or impurities.

Synthetic primary and secondary proteins are generally prepared by chemical synthesis utilizing techniques known in the art and generally mimic the equivalent natural protein's or natural protein derivative's chemical and/or structural makeup. Furthermore, individual proteins may be chemically combined with one or more other proteins of the same or different type to produce a dimer, trimer or other multimer. A simple advantage of having a larger protein molecule is that it will make interconnections with other protein molecules to create a stronger coacervate or biomaterial that is less susceptible to dissolving in aqueous solutions and provides additional protein structural and biochemical characteristics.

Additionally, protein molecules can also be chemically combined to any other chemical so that the chemical does not release from the biocoacervate or biomaterial. In this way, the chemical entity can provide surface modifications to the biocoacervate or biomaterial or structural contributions to the biocoacervate or biomaterial to produce specific characteristics. The surface modifications can enhance and/or facilitate cell attachment depending on the chemical substance or the cell type. The structural modifications can be used to facilitate or impede dissolution or enzymatic degradation of the biocoacervate or biomaterial, as well as increase the affinity of the biocoacervate to interact (e.g. bind or coat) with other materials.

Synthetic biocompatible proteins may be cross-linked, linked, bonded, chemically and/or physically linked to pharmacological active agents, enzymatically, chemically or thermally cleaved and utilized alone or in combination with other biocompatible proteins or partial proteins e.g. peptides, to form the biocoacervates or biomaterials. Examples of such synthetic biocompatible proteins include, but are not limited to heparin-protein, heparin-polymer, chondroitin-protein, chondroitin-polymer, heparin-cellulose, heparin-alginate, heparin-polylactide, GAGs-collagen, heparin-collagen, collagen-elastin-heparin, collagen-albumin, collagen-albumin-heparin, collagen-albumin-elastin-heparin, collagen-hyaluronic acid, collagen-chondroitin-heparin, collagen-chondroitin and the like.

A specific example of a particularly preferred genetically engineered primary protein for use in the biocoacervates or biomaterials of the present invention is human collagen produced by FibroGen, Inc., 225 Gateway Blvd., South San Francisco, Calif. 94080. Other examples of particularly preferred genetically engineered proteins for use in the biocoacervates or biomaterials of the present invention are commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
|---|---|
| SLP 3 | [(GAGAGS)$_9$ GAAGY)](Referred to herein as SEQ ID NO: 1) |
| SLP 4 | (GAGAGS)$_n$ (Referred to herein as SEQ ID NO: 2) |
| SLP F | [(GAGAGS)$_9$ GAA VTGRGDSPAS AAGY]$_n$ (Referred to herein as SEQ ID NO: 3) |
| SLP L3.0 | [(GAGAGS)$_9$ GAA PGASIKVAVSAGPS AGY]$_n$ (Referred to herein as SEQ ID NO: 4) |
| SLP L3.1 | [(GAGAGS)$_9$ GAA PGASIKVAVSGPS AGY]$_n$ (Referred to herein as SEQ ID NO: 5) |
| SLP F9 | [(GAGAGS)$_9$ RYVVLPRPVCFEK AAGY]$_n$ (Referred to herein as SEQ ID NO: 6) |

TABLE A -continued

Protein polymer sequences

| Polymer Name | Monomer Amino Acid Sequence |
|---|---|
| ELP I | [(VPGVG)$_4$]$_n$ (Referred to herein as SEQ ID NO: 7) |
| SELP 0 | [(GVGVP)$_8$ (GAGAGS)$_2$]$_n$ (Referred to herein as SEQ ID NO: 8) |
| SELP 1 | [GAA (VPGVG)$_4$ VAAGY (GAGAGS)$_9$]$_n$ (Referred to herein as SEQ ID NO: 9) |
| SELP 2 | [(GAGAGS)$_6$ GAAGY (GAGAGS)$_5$ (GVGVP)$_8$]$_n$ (Referred to herein as SEQ ID NO: 10) |
| SELP 3 | [(GVGVP)$_8$ (GAGAGS)$_8$]$_n$ (Referred to herein as SEQ ID NO: 11) |
| SELP 4 | [(GVGVP)$_{12}$ (GAGAGS)$_8$]$_n$ (Referred to herein as SEQ ID NO: 12) |
| SELP 5 | [(GVGVP)$_{16}$ (GAGAGS)$_8$]$_n$ (Referred to herein as SEQ ID NO: 13) |
| SELP 6 | [(GVGVP)$_{32}$ (GAGAGS)$_8$]$_n$ (Referred to herein as SEQ ID NO: 14) |
| SELP 7 | [(GVGVP)$_8$ (GAGAGS)$_6$]$_n$ (Referred to herein as SEQ ID NO: 15) |
| SELP 8 | [(GVGVP)$_8$ (GAGAGS)$_4$]$_n$ (Referred to herein as SEQ ID NO: 16) |
| KLP 1.2 | [(AKLKLAEAKLELAE)$_4$]$_n$ (Referred to herein as SEQ ID NO: 17) |
| CLP 1 | [GAP(GPP)$_4$]$_n$ (Referred to herein as SEQ ID NO: 18) |
| CLP 2 | {[GAP(GPP)$_4$]$_2$ GPAGPVGSP}$_n$ (Referred to herein as SEQ ID NO: 19) |
| CLP-CB | {[GAP(GPP)$_4$]$_2$ (GLPGPKGDRGDAGPKGADGSPGPA) GPAGPVGSP}$_n$ (Referred to herein as SEQ ID NO: 20) |
| CLP 3 | (GAPGAPGSQGAPGLQ)$_n$ (Referred to herein as SEQ ID NO: 21) |

Repetitive amino acid sequences of selected protein polymers.
SLP = silk like protein;
SLPF = SLP containing the RGD sequence from fibronectin;
SLPL 3/0 and SLPL 3/1 = SLP containing two difference sequences from laminin protein;
ELP = elastin like protein;
SELP = silk elastin like protein;
CLP = collagen like protein;
CLP-CB = CLP containing a cell binding domain from human collagen;
KLP = keratin like protein The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The biocoacervates and biomaterials utilized in various embodiments of the present invention also include one or more glycosaminoglycans, proteoglycans or mucopolysaccharides. Glycosaminoglcans can be derived or synthesized from any source, including artificial, animal or plant sources. Examples of glycosaminoglycans that are utilized in the coacervates and biomaterials of the present invention include but are not limited to the heparin, heparin sulfate, keratan sulfate, dermatin, dermatin sulfate, heparin-hyaluronic acid, chondroitin, chondroitin sulfate (e.g. chondroitin 6-sulfate and chondroitin 4-sulfate), chitin, chitosan, acetyl-glucosamine, hyaluronic acid, aggrecan, decorin, biglycan, fibromodulin, lumican, combinations, glycosaminoglycan complexes or compounds and the like.

The biocoacervates and biomaterials utilized in various embodiments of the present invention also include one or more biocompatible solvents. Any biocompatible solvent may be utilized in the method and corresponding coacervate or biomaterial of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); biocompatible alcohols, such as polyols, glycerol, methanol and ethanol; various acids, such as acetic acid, citric acid, ascorbic acid and formic acid; oils, such as olive oil, peanut oil and the like; glycols, such as ethylene glycol; and combinations of these and the like. Preferably, the biocompatible solvent comprises water. The amount of biocompatible solvent utilized in the formation of the present invention will preferably be that amount sufficient to result in the primary and secondary proteins being fluid and flowable enough to allow the protein to enter into solution. Generally, the amount of biocompatible solvent suitable for use in the method of the present invention will range from about 100% to about 50,000% by weight, in some embodiments from about 200% to about 10,000% by weight, and in other embodiments from about 300% to about 2000% by weight, based upon the weight and/or amount of the protein utilized.

In addition to the biocompatible protein(s) and the biocompatible solvent(s), the coacervates or biomaterial that may be utilized in various embodiments of the present invention may include one or more pharmacologically active agents. Generally, the distribution of the pharmacologically active agent is rendered substantially homogenous throughout the resulting coacervate or biomaterial. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the coacervates, biomaterials and the vessel graft systems and its components of the present invention include, but are not limited to, (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhythmics such as amiodarone, flecamide, disopyramide, procainamide, mexiletene and quinidine, Antiangina agents such as glyceryl trinitrate, erythrityl tetranitrate, pentaerythritol tetranitrate, mannitol hexanitrate, perhexylene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, actinomycin D, sirolimus, tacrolimus, everolimus, estradiol and dexamethasone;

Antimigraine preparations such as ergotanmine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papavereturn, pentazocine, pethidine, phenopefidine, codeine dihydrocodeine; acetylsalicylic acid (aspirin), paracetamol, and phenazone;

Immunosuppressants, antiproliferatives and cytostatic agents such as rapomycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexyl, procyclidine and dopamine-2 agonists such as S (−)-2-(N-propyl-N2-thienylethylamino)-5-hydroxytetralin (N-0923), Anticonvulsants such as phenyloin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;
Antioestrogens such as tamoxifen and epitiostanol and the aromatase inhibitors, exemestane and 4-hydroxy-androstenedione and its derivatives;
Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;
5-alpha reductase inhibitors such as finasteride, turosteride, LY-191704 and MK-306;
Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;
Complex carbohydrates such as glucans;
Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluorometholone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;
Pituitary hormones and their active derivatives or analogs such as corticotrophin, thyrotropin, follicle stimulating hormone (FSH), luteinising hormone (LH) and gonadotrophin releasing hormone (GnRH);
Hypoglycemic agents such as insulin, chlorpropamide, glibenclamide, gliclazide, glipizide, tolazamide, tolbutamide and metformin;
Thyroid hormones such as calcitonin, thyroxine and liothyronine and antithyroid agents such as carbimazole and propylthiouracil;
Other miscellaneous hormone agents such as octreotide;
Pituitary inhibitors such as bromocriptine;
Ovulation inducers such as clomiphene;
Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;
Antidiuretics such as desmopressin, lypressin and vasopressin including their active derivatives or analogs;
Obstetric drugs including agents acting on the uterus such as ergometrine, oxytocin and gemeprost;
Prostaglandins such as alprostadil (PGE1), prostacyclin (PGI2), dinoprost (prostaglandin F2-alpha) and misoprostol;
Antimicrobials including the cephalosporins such as cephalexin, cefoxytin and cephalothin;
Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;
Tetracyclines such as minocycline, chlortetracycline, tetracycline, demeclocycline, doxycycline, methacycline and oxytetracycline and other tetracycline-type antibiotics;
Amnioglycoides such as amikacin, gentamicin, kanamycin, neomycin, netilmicin and tobramycin;
Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;
Quinolones such as nalidixic acid, cinoxacin, ciprofloxacin, enoxacin and norfloxacin;
Sulphonamides such as phthalysulphthiazole, sulfadoxine, sulphadiazine, sulphamethizole and sulphamethoxazole;
Sulphones such as dapsone;
Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, timidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;
Antituberculosis drugs such as ethambutol, isoniazid, pyrazinamide, rifampicin and clofazimine;
Antimalarials such as primaquine, pyrimethamine, chloroquine, hydroxychloroquine, quinine, mefloquine and halofantrine;
Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;
Anthelmintics such as mebendazole, thiabendazole, niclosamide, praziquantel, pyrantel embonate and diethylcarbamazine;
Cytotoxic agents such as plicamycin, cyclophosphamide, dacarbazine, fluorouracil and its prodrugs (described, for example, in *International Journal of Pharmaceutics,* 111, 223-233 (1994)), methotrexate, procarbazine, 6-mercaptopurine and mucophenolic acid;
Anorectic and weight reducing agents including dexfenfluramine, fenfluramine, diethylpropion, mazindol and phentermine;
Agents used in hypercalcaemia such as calcitriol, dihydrotachysterol and their active derivatives or analogs;

Antitussives such as ethylmorphine, dextromethorphan and pholcodine; Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine, bupivacaine, amethocaine, lignocaine, lidocaine, cocaine, cinchocaine, dibucaine, mepivacaine, prilocalne, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.*, 106(5), 1096, (1996)];

Neuromuscular blocking agents such as suxamethonium, alcuronium, pancuronium, atracurium, curarie, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, B12α., and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Bone and/or tissue mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides.

Additionally, the coacervates and biomaterials of the present invention are particularly advantageous for the encapsulation, incorporation and/or scaffolding of macromolecular pharmacologically active agents such as pharmacologically active proteins, enzymes, peptides, polysaccharides, nucleic acids, cells, tissues, and the like. It is noted that the encapsulation of certain pharmacologically active agents with the biocoacervate or biomaterial of the present invention reduces, if not prevents, the potential for undesirable reaction with bodily fluids or tissues that may otherwise occur upon implantation of a reactive drug delivery device without protective encapsulation. Immobilization of macromolecular pharmacologically active agents into or onto biomaterials can be difficult due to the ease with which some of these macromolecular agents denature when exposed to organic solvents, some constituents present in bodily fluids or to temperatures appreciably higher than room temperature. However, since the method of the present invention utilizes biocompatible solvents such as water, DMSO or ethanol the risk of the denaturation of these types of materials is reduced. Furthermore, due to the size of these macromolecular pharmacologically active agents, these agents may be encapsulated within the coacervates or biomaterials of the present invention and thereby are protected from constituents of bodily fluids that would otherwise denature them. Thus, the coacervates and biomaterials of the present invention allow these macromolecular agents to exert their therapeutic effects, while yet protecting them from denaturation or other structural degradation. Also, embodiments of the present invention include coacervates or biomaterials that provide presentation of therapeutic moieties of attached or residing compounds, cells and the like to the biological surroundings.

Examples of cells which can be utilized as the pharmacologically active agent in the coacervates, biomaterials and related devices of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, endothelial cells, epithelial cells, hepatocytes, T-cells, combinations of these, and the like. As can be seen from this partial list, cells of all types, including dermal, neural, blood, organ, stem, muscle, glandular, reproductive and immune system cells, as well as cells of all species of origin, can be encapsulated and/or attached successfully by this method.

Examples of pharmacologically active proteins which can be incorporated into the coacervates or biomaterials of the present invention include, but are not limited to, hemoglobin, bone morphogenic protein, desmopressin, vasporessin, oxytocin, adrenocorticocotrophic hormone, epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies, such as herceptin and rituximab; vitamins; cofactors; growth factors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR-52ed (1998)—Medical Economics 1974. In consideration of these parameters, it has been found that a wide range exists in the amount of the pharmacologically active agent(s) capable of being incorporated into and subsequently released from or alternatively allowed to exert the agent's therapeutic effects from within the coacervates or biomaterials. More specifically, the amount of pharmacologically active agent that may be incorporated into and then either released from or active from within the coacervates or biomaterials may range from about 0.001% to about 60%, in various embodiments from about 0.05% to about 40%, and in some embodiments from about 0.1% to 20%, based on the weight of the coacervate material or biomaterial. It is important to note that the pharmacologically active agents are generally homogenously distributed throughout the coacervate material or biomaterial thereby allowing for a controlled release of these agents.

The one or more pharmacologically active agents can be included in one or more components of the vessel graft system of the present invention. For example, the vessel graft system may include pharmacologically active agents included in the vessel or tube, the suture or thread, the bioglue or adhesive or in any combination of these components. In various examples of the present invention the ends of the tube includes one or more agent(s) (e.g. sirolimus or rapamycin) or the suture or thread includes the one or more agent(s) (e.g. paclitaxel or rapamycin). In yet other embodiments, the bioglue or adhesive includes the one or more agent(s). In yet other embodiments, one or more of the above components (e.g. tube, thread or bioglue) includes the one or more agent(s).

Finally, one or more additive materials may be added to the coacervate or biomaterial to manipulate the material properties and thereby add additional structure, enhance absorbance of the pharmacologically active agents, enhance membrane permeation by pharmacologically active agents (cell and tissue), enhance mucoadhesion or modify the release of pharmacologically active agents. That is, while a coacervate material or biomaterial that includes a relatively fast-degrading protein material without a particular additive material may readily degrade thereby releasing drug relatively quickly upon insertion or implantation, a coacervate material or biomaterial that includes a particular polymeric material, such as polyanhydride, will degrade slowly, as well as release the pharmacologically active agent(s) over a longer period of time. Examples of biodegradable and/or biocompatible additive materials suitable for use in the coacervate or biomaterial of the present invention include, but are not limited to polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyethyl vinyl acetate (PEVA), polyacetal, poly(lactic acid), poly(ethylene oxide)/poly(butylene terephthalate) copolymer, polycarbonate, poly(tetrafluoroethylene) (PTFE), polycaprolactone, polyethylene oxide, polyethylene glycol, poly (vinyl chloride), polylactic acid, polyglycolic acid, polypropylene oxide, poly(alkylene)glycol, polyoxyethylene, sebacic acid, polyvinyl alcohol (PVA), 2-hydroxyethyl methacrylate (HEMA), polymethyl methacrylate, polybutyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, glycosaminoglycans such as hyaluronic acid or chondroitin sulfate, bioceramic materials such as hydroxyapetite, graphite, flexible fluoropolymer, isobutyl-based, isopropyl styrene, vinyl pyrrolidone, cellulose acetate dibutyrate, silicone rubber, copolymers of these, and the like.

Additionally, hydrophobic additives such as lipids can be incorporated into the coacervates or biomaterials to extend the duration of drug release or facilitate the incorporation of hydrophobic drugs. Exemplary hydrophobic substances include lipids, e.g., tristearin, ethyl stearate, phosphotidycholine, polyethylene glycol (PEG); fatty acids, e.g., sebacic acid erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4.

Alternatively hydrophilic additives may be added to the coacervates or biomaterials of the present invention to provide desirable characteristics, such as expedite delivery of the drugs or facilitate the addition of other hydrophilic substances. Exemplary hydrophilic additives useful to shorten the release duration of the pharmacologically active agent include but are not limited to, salts, such as sodium chloride; and amino acids, such as glutamine and glycine.

Other additive materials that may be incorporated into the biocoacervates or biomaterials of the present invention to provide enhanced features include, but are not limited to, insoluble proteins (e.g. collagen, elastin . . . ), ceramics, bioceramics, glasses, bioglasses, glass-ceramics, resin cement, resin fill; more specifically, glass ionomer, calcium sulfate, $Al_2O_3$, tricalcium phosphate, calcium phosphate salts, sugars, lipoproteins, starches, ferrous salts and compounds, carbohydrates, salts, polysaccharides, carbon, magnetic particles, fibers or other magnetic substances, humectants or mucoadhesive enhancers such as glycerol and alginate, absorption or membrane permeation enhancers such as ascorbic acid, citric acid and Lauroylcarnitine. Additional other materials that may be incorporated into the coatable composition include alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

Additionally other biocoacervate or biomaterial embodiments include a biocoacervate or biomaterial vessel graft system that has incorporated into it a marker system that allows the device to be located and imaged using ultrasound, MRI, X-Ray, PET or other imaging techniques. The image marker can be made with air bubbles or density materials that allow easy visualization of the system by ultrasound. The incorporated materials can be metallic, gaseous or liquid in nature. Specific materials that may be utilized as image markers incorporated into the biocoacervate or biomaterial vessel graft systems include, but are not limited to, Gd-DPTA. It may be possible to cause the biocoacervate or biomaterial to react to an imaging technique, i.e., ultrasound to make bubbles or through the addition of another chemical or substance to the system (e.g., peroxide addition to a biocoacervate or biomaterial that contains peroxidase as an intrauterine marker that can be monitored by ultrasound). Also, the addition of a harmless unique salt solution, or enzyme, may promote gas production by the biocoacervate or biomaterial as an ultrasound maker. The biocoacervate or biomaterial of the present invention can contain agents that can be seen by ultrasound, MRI, PET, x-ray or any imaging device that is either known, in development or developed in the future.

The additives may be added at any time during the preparation of the coacervate or biomaterial. For example additives, such as particles or fibers (drugs, insoluble proteins, hydroxy apetite . . . ), macromolecules (DNA, proteins, peptides, glycosaminoglycans (e.g. hyaluronic acid, chondroiten sulfate) . . . ), small molecules (NSAIDS, Sufentanil, Sirolimis, Paclitaxel, Estradiol, Capsaicin . . . ), combininations thereof and the like may be added to the protein solution or may be added to the molten coacervate. Such addition has the benefit of distributing the additive homogeneously throughout the coacervate or biomaterial.

If additives are to be incorporated into the coacervates or biomaterials of the present invention, they will preferably be included in an amount so that the desired result of the additive is exhibited. Generally, if included in embodiments of the biocoacervate of the present invention, the amount of additives may vary between from about 0.001% to about 60%, in various embodiments from about 0.05% to 30% by weight, and in some embodiments from about 0.1% to 10% by weight based upon the weight of the biocoacervate or biomaterial.

One method of producing the biocoacervate of the present invention is by providing one or more selected soluble or solubilized primary proteins, such as collagen, laminin or fibronectin and, in various embodiments, one or more soluble or solubilized secondary proteins such as elastin or albumen. The primary and secondary proteins are added to a sufficient amount of biocompatible solvent, preferably water, under heat until the proteins are substantially dissolved in the solvent (e.g. >50% dissolved and in some embodiments>75% dissolved). The proteins are added to the solvent that is generally heated to approximately 30-150° C., in various embodiments from about 40-90° C., and in some embodiments from about 40-70° C. thereby producing a protein solution. Once the protein solution is formed, one or more glycosaminoglycans, such as heparin, chondroitin sulfate or hyaluronic acid are added to the protein solution thereby forming an amorphous coacervate, which drops out of the solution. It is noted that before adding the one or more glycosaminoglycans to the protein solution one or more other materials (pharmacologically active agents, additives, etc.) may be added to the one or more heated solvents (water) while stirring. It is also noted that the secondary proteins may dissolved in a solution separate from the primary protein (e.g. the same solution as the glycosaminoglycan) and added to the primary protein solution prior to or with the solution including the glycasaminoglycan. Once the coacervate has dropped out of solution, the solution and coacervate are normally allowed to cool to at about 0-35° C., in various embodiments from about 10-25° C., and in some embodiments from about 17-22° C. and the solution is poured off the coacerate or the coacervate is extracted from the solution.

Figure 3:
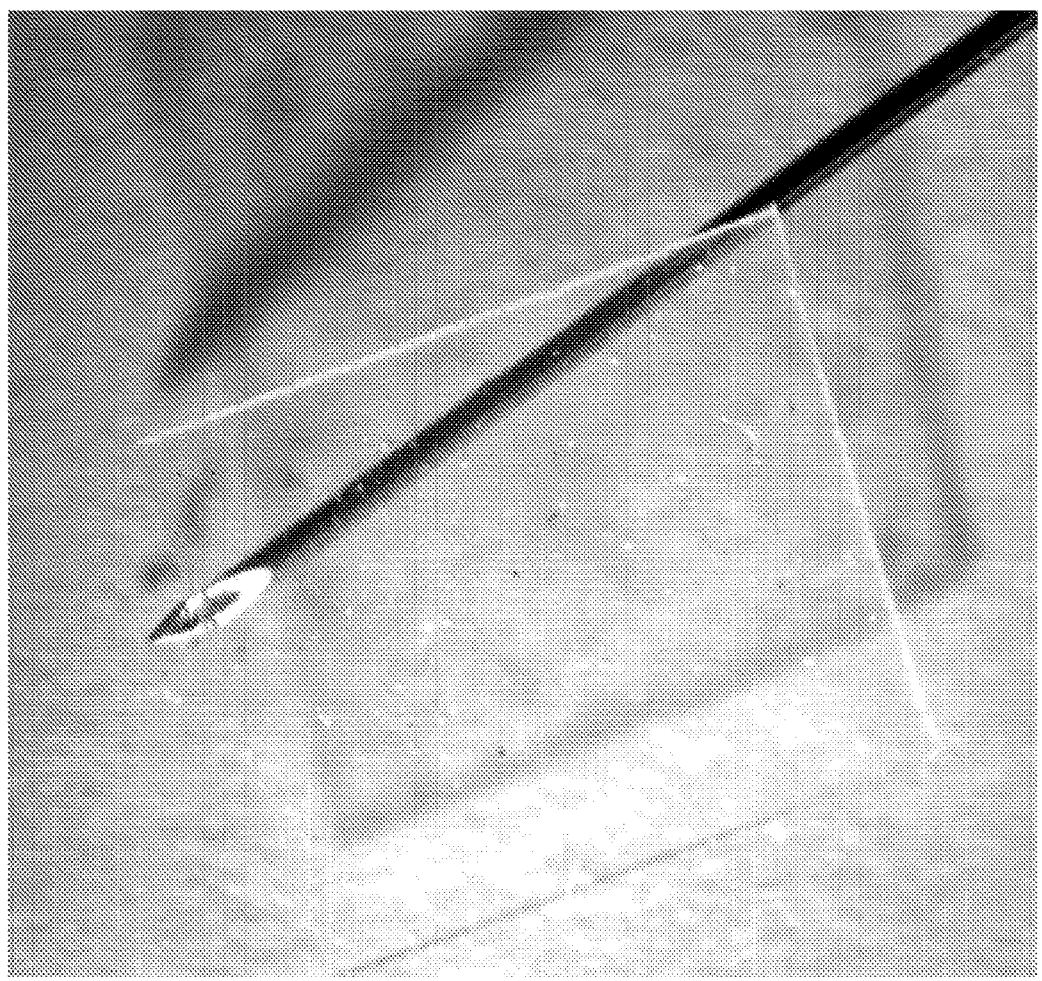
FIG. 3 depicts one embodiment of the biocoacervate of the present invention cut into a square shape.

Many embodiments of the biocoacervate and biomaterials of the present invention are thermoplastics, thereby possessing thermoplastic chemical and mechanical characteristics. Therefore, the biocoacervates and some embodiments of the biomaterials have the property of softening/melting when heated and of hardening again when cooled; these thermoplastic materials can be remelted and cooled time after time without undergoing any substantial chemical change. In view of these thermoplastic characteristics, various embodiments of the formed biocoacervate may be reformed into any shape and size by simply heating the biocoacervate until it melts and forms a liquid. The melted biocoacervate may also be utilized to coat materials in the systems of the present invention, such as tube scaffolding and threads. Generally, the biocoacervate can be melted at a temperature from about 20-120° C., in various embodiments from about 25-80° C., in some embodiments from about 30-65° C. Next, the melted biocoacervate may be poured into a cast or mold or spray or dip coated onto a scaffolding or thread or other material and allowed to cool, thereby resolidifying and reforming into the desired shape and/or size. FIG. 3 depicts an example of the biocoacervate of the present invention formed into a square shape. It is noted that at various levels of crosslinking the thermoplastic characteristics of some of the embodiments of the present invention may diminish or be eliminated.

It is noted that in forming the protein solution, the primary and secondary proteins, the biocompatible solvent(s), and optionally the pharmacologically active agent(s) and additive(s) may be combined in any manner. For example, these components may simply be combined in one step, or alternatively, the primary and secondary protein materials may be dissolved in one or multiple biocompatible solvents and an additional protein material, pharmacologically active agent and/or additive may be dissolved and/or suspended in the same or another biocompatible solvent. Once the components are placed into one or more solutions, the resulting solutions may be mixed to precipitate the amorphous biocoacervate.

Once the coacervate is formed, it may be optionally pressed or vacuumed to further form, modify, set the configuration and/or remove any excess solvent or air trapped within the biocoacervate. It is noted that the resulting coacervate may be melted and placed in vacuum to remove any excess air trapped within the coacervate. The pressing may also be performed when a melted coacervate is resetting to a solid state by pouring the melted coacervate in a mold and applying pressure while cooling. The biocoacervate may optionally be dried to reduce water content to transform the coacervate gel-like structure into more of a cohesive body material to allow it to accept compression. Any manually or automatically operable mechanical, pneumatic, hydraulic, or electrical molding device capable of subjecting the coacervate to pressure is suitable for use in the method of the present invention. In the production of various embodiments of the present invention, a molding device may be utilized that is capable of applying a pressure of from about 100 pounds per square inch (psi) to about 100,000 psi for a time period of from about one (1) seconds to about forty-eight (48) hours. Preferably, the molding device used in the method of the present invention will be capable of applying a pressure of from about 1000 psi to about 30,000 psi for a time period of from about two (2) seconds to about sixty (60) minutes. More preferably, the molding device used in the method of the present invention will be capable of applying a pressure of from about 3,000 psi to about 25,000 psi for a time period of from about three (3) seconds to about ten (10) minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available. See U.S. Pat. No. 6,342,250 and U.S. application Ser. No. 09/796,170, which are incorporated by reference herein, for a description of one type of compression molding device that may be utilized in the process of the present invention.

As previously indicated, the biocoacervate of the present invention is not soluble in water at room temperature. However, the coacervate does dissolve in saline solution or other physiological solutions. A biocoacervate or biomaterial that does not dissolve in saline solution or other physiological solutions may be produced by setting the biocoacervate in the desired configuration and size by utilizing a crosslinking technique. It is also noted that various crosslinking reagents, techniques and degrees of crosslinking manipulate the melting point of the crosslinked material and its physical and biological characteristics. It has been found that the application of crosslinking to the biocoacervate will generally tend to raise the melting point of the biocoacervate.

Many crosslinking techniques known in the art may be utilized to set the biocoacervate into the desired configuration (e.g. tubular shape, thread shape . . . ), thereby forming a biomaterial that does not dissolve in saline solution. For example, embodiments of the biocoacervate may be crosslinked by reacting the components of the biocoacervate with a suitable and biocompatible crosslinking agent. Crosslinking agents include, but are not limited to glutaraldehyde, p-Azidobenzolyl Hydazide, N-5-Azido-2-nitrobenzoyloxy-succinimide, 4-[p-Azidosalicylamido]butylamine, glycidyl ethers such as 1,4-butandiol diglycidylether, any other suitable crosslinking agent and any combination thereof. A description and list of various crosslinking agents and a disclosure of methods of performing crosslinking steps with such agents may be found in the Pierce Endogen 2001-2002 or 2003-2004 Catalog which is hereby incorporated by reference. It is also noted that multiple applications of crosslinking agents at different stages may produce desired products.

Furthermore, it is noted that embodiments of the coacervates of the present invention may include crosslinking reagents that may be initiated and thereby perform the crosslinking process by UV light activation or other radiation source, such as ultrasound or gamma ray or any other activation means.

The protein biocoacervate may also be crosslinked by utilizing other methods generally known in the art. Also, the biocoacervate may be crosslinked when in a solid state or crosslinking agent(s) may be added when the biocoacervate is in a melted state (e.g. bioglue or adhesive). For example, the coacervates of the present invention may be partially or entirely crosslinked by exposing, contacting and/or incubating a coacervate with a gaseous crosslinking reagent, liquid crosslinking reagent, light, heat or combination thereof. In various embodiments of the present invention the coacervate may be crosslinked by contacting the coacervate with a liquid crosslinking reagent, such as glutaraldehyde or 1,4-butandiol diglycidylether. In one preferred embodiment of the present invention the coacervate is crosslinked in a solution of approximately 0.01%-50% gluteraldehyde. Additionally, it is noted that in processes including a crosslinking agent the coacervate is generally exposed to the crosslinking agent for a period of about 1 min to 24 hours, in various embodiments from about 5 min. and 6 hours and in some embodiments from about 15 min. and 3 hours.

Embodiments of the present invention may also include the addition of reagents to properly pH the resulting coacervate, biomaterial and related devices of the present invention. These pH reagents may be added to the coacervate during formation of the coacervate, exposing the formed coacervate to a solution of the desired pH or adjusting the pH when the coacervate is in a melted state. The appropriate adjustment of pH thereby enhances the biocompatible characteristics of the biomaterials with the host tissue of which it is to be administered and may also act to stabilize the material in physiologic conditions. When preparing the coacervate, the pH reagents are generally added to the protein solution prior to addition of the glycosaminoglycans. However, the pH reagent may alternatively be added after the amorphous coacervate is formed. For example the pH reagent may be added to the melted form of the coacervate in the attempt to obtain the proper pH levels. In various embodiments of the present invention, the adjustment of pH can be performed by the addition of drops of about 0.05N to 4.0N acid or base to the protein solution or melted coacervate until the desired pH is reached as indicated by a pH meter, pH paper or any pH indicator. In various embodiments, the addition of drops of about 0.1N-0.5 N acid or base are used. Although any acid or base may be used, the preferable acids and bases are HCl and KOH, NaOH or combinations thereof, respectively. It has been found that adjusting the pH at or between about 4 and 9, and in many embodiments at or between about 6 and 8, have provided beneficial materials.

The resulting biocoacervate preferably has the maximum solvent amount absorbable with as little excess solvent as possible while still being structured into a shape-holding amorphous solid and possessing the desired features relevant to the material's and/or device's function, e.g., preferably a solvent content of from about 20% to about 90%, in various embodiments a solvent content of from about 30% to about 80% and in some embodiments from about 40% to 75%. Additionally, the amount of proteins and glycosaminoglycan found in the resulting coacervate or biomaterial may vary from about 10% to about 80%, in some embodiments from about 20% to 70% by weight, and in other embodiments from about 25% to 60% by weight based upon the weight of the resulting biocoacervate or biomaterial. The amount of glycosaminoglycan present in various embodiments of the present invention generally is about 3% to about 25%, in some embodiments about 5% to 20% by weight, and in other embodiments about 8% to 15% by weight based upon the weight of the protein included in the biocoacervate.

Since biocompatible proteins and solvents are used in the manufacture of the biocoacervates, biomaterials and vessel graft devices of the present invention, the potential for adverse tissue reactions to foreign substances, such as chemical solvents are reduced, if not substantially precluded. For all of these reasons, the coacervates and biomaterials in accordance with the present invention may advantageously be used to effect a local therapeutic result in a patient in need of such treatment. More specifically, the vessel graft systems of the present invention that include such biocoacervates and biomaterials may be implanted or administered in a patient to illicit a therapeutic effect either locally or systemically. For example, depending on the desired therapeutic effect, the coacervates or biomaterials may be used to regenerate tissue, repair tissue, replace tissue, and deliver local and systemic therapeutic effects such as anti-proliferation, analgesia or anesthesia, or alternatively, may be used to treat specific conditions, such as coronary artery disease, heart vessel failure and neural tissue defects or trauma. The coacervates or biomaterials that include pharmacologically active agents may be utilized in instances where long term, sustained, controlled release of pharmacologically active agents is desirable, such as in the treatment of surgical and post-operative pain, extended tissue regeneration and/or healing or other conditions requiring chronic pain management.

The patient to which the vessel graft systems are administered may be any patient in need of a therapeutic treatment. Preferably, the patient is a mammal, reptile or bird. More preferably, the patient is a human. Furthermore, the vessel graft systems and its respective components (e.g. tube, sutures, biomesh, bioglue . . . ) can be implanted in any location to which it is desired to effect a local therapeutic response. For example, the coacervates, biomaterials or related vessel graft devices may be administered, applied, sutured, clipped, stapled, injected and/or implanted. Furthermore, implanted coacervate/biomaterial vessel graft systems and its components may absorb water and swell, thereby assisting the coacervates, biomaterials or related devices to stay substantially in the location where it was implanted or injected.

The present invention will now be further described with reference to the following non-limiting examples of the vessel graft systems, the components of the systems and the following materials and methods that are employed to make and use the systems. It is noted that any additional features presented in other embodiments described herein may be incorporated into the various embodiments being described.

Vessel Graft Systems:

As previously suggested, various embodiments of the vessel graft systems of the present invention include the following components: 1) one or more vessels and/or tubes; 2) one or more sutures or threads; and 3) in some embodiments one or more adhesives or bioglues. It is noted that any or all of the components may include the previously described biocoacervates and biomaterials of the present invention. Furthermore, the components utilized in the vessel graft systems of the present invention may be administered without drugs or may include one or more pharmacologically active agents to provide a therapeutic effect.

In various embodiments of the present invention, the vessel may be manufactured from and/or include one or more biocoacervates and/or biomaterials as described above. Upon implantation, the vessel may be sutured to a native vessel with a suture that includes one or more pharmacologically active agents and is made from or is coated or encapsulated with the biocoacervate or biomaterial of the present invention. Alternatively, the suture, thread or a wrap including the one or more pharmacologically active agents may be wrapped around one or more ends of the vessel upon the implanting of the vessel to deliver the agent(s). Such positioning of the suture or thread including the drug(s) allows for the delivery of such agents (e.g. paclitaxel or rapamycin) thereby inhibiting the growth of tissue into the lumen of the vessel at the anastomosis site. It is noted that the vessel graft may be inserted into the anastomosis sites of the native vessel and then secured.

In yet other embodiments the vessel may be formed from and/or include the biocoacervate and/or biomaterial may be secured to the native vessel upon implantation with one or more bioglues or adhesives made from the biocoacervate of the present invention. In yet other embodiments the vessel graft system may include a vessel that includes a thread or suture positioned at one or more ends that is sealed into position with one or more bioglues of the present invention. A description of how to make embodiments of the components used in the vessel graft systems of the present invention and how each is used in various vessel graft systems is explained further below.

It is noted that the controlled release characteristics of the vessel, suture and/or bioglue that includes one or more pharmacologically active agent(s) provides for a greater efficiency in the delivery of pharmacologically active agent(s) that are incorporated into the biocoacervate or biomaterial. The controlled release of pharmacologically active agent, if present, is partially attributed to the homogenous distribution of the pharmacologically active agent(s) throughout the biocoacervate or biomaterial. This homogenous distribution provides for a more systematic, sustainable and consistent release of the pharmacologically active agent(s) by gradual degradation of the coacervate or material or by diffusion of the pharmacologically active agent(s) out of the coacervate or material. As a result, the release characteristics of the pharmacologically active agent from the biocoacervate, biomaterial and/or device are enhanced.

Additionally, as previously mentioned, other optional biocompatible additives, if included in the coacervate or biomaterial, will be compelled and influenced to interact with the various components, including the pharmacologically active agents if present, to augment their biodurability, biocompatibility and/or drug release characteristics if drugs are present in the materials. Augmentation may include inhibiting or enhancing the release characteristics of the pharmacologically active agent(s), if present. For example, a multi-layered vessel or tube may comprise alternating layers of biocoacervates or biomaterials that have sequential inhibiting and enhancing biocompatible additives included, thereby providing a pulsing release of pharmacologically active agents. A specific example may be utilizing glutamine in a layer as an enhancer and polyanhydride as an inhibitor. The inhibiting layer may include drugs or no drugs.

A. Vessel Grafts:

In various embodiments of the present invention the biocoacervates and/or biomaterials explained above may be used in producing the components of the vessel grafts of the present invention such as vessels (e.g. tubular grafts such as tracheal tubes, bronchial tubes, catheter functioning tubes, blood vessels . . . ), vessel fasteners (e.g. sutures, threads, staples . . . ) and bioglues or adhesives. It is noted that a tube does not necessarily have to be cylindrical in shape, but is generally found in that configuration.

Figure 4A:
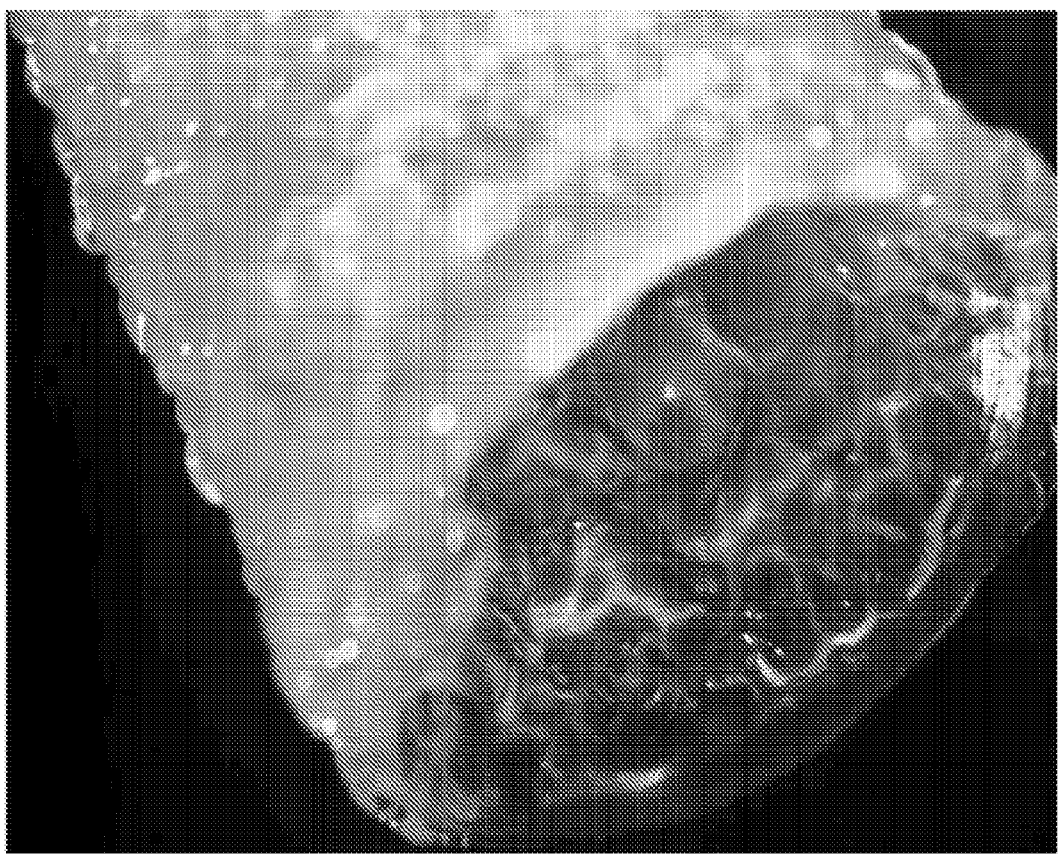
FIGS. 4A and 4B depict another embodiment of a vessel of the present invention that has been implanted and wherein the scaffolding material is a cotton knit.

In various component embodiments of the vessel graft systems of the present invention the biocoacervate or biomaterial may be coated or impregnated onto or into a scaffolding type structure, such as a polyurethane foam tube, mesh or thread; methacrylate meshing, tube, foam or thread; nylon meshing, tube or thread, polypropylene/polytetrafluoroethylene meshing, tube or thread; cotton knitted material, meshing, tube or thread; Dacron knitted material, meshing, tube or thread; polytetrafluoroethylene meshing, tube or thread; silk meshing, tube or thread; and Teflon meshing, tube or thread. One embodiment of a scaffolding type structure that may be used in manufacturing tubes use in the systems of the present invention is a polypropylene/polytetrafluoroethylene mesh tube, such as that produced by Secant, Inc. In one embodiment of the present invention, as depicted in FIG. 4A, a vessel is prepared by applying the melted biocoacervate to a polypropylene/polytetrafluoroethylene mesh tube and supplying vacuum to remove trapped air within the pores of the tube. It is noted that in other embodiments of the present invention, the scaffolding structure of the vessel graft may be a cotton tube or a polyurethane foam tube rather than the a polypropylene/polytetrafluoroethylene mesh tube.

Figure 4B:
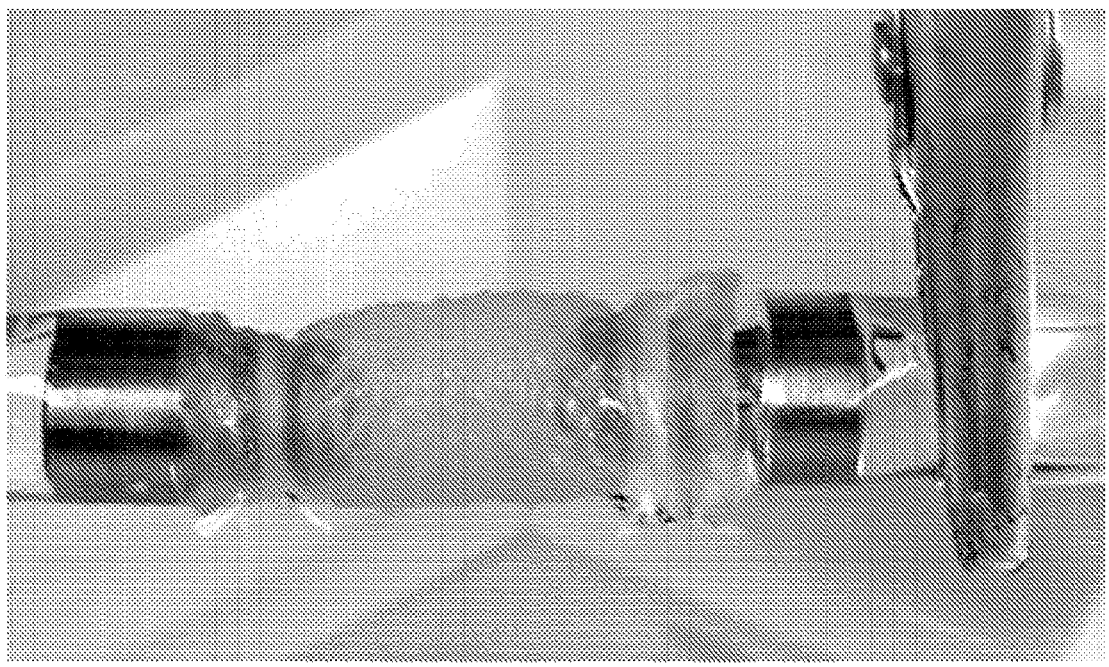

Finally, FIG. 4B depicts the vessel graft including a polypropylene/polytetrafluoroethylene mesh tube that has been placed under hydrostatic pressure of over 200 psi for greater than 3 days.

The melted biocoacervate may be applied to the scaffolding structure, such as a polyurethane, polypropylene/polytetrafluoroethylene or knit cotton tube, by any process known in the art such as painting, injection molding, dip coating, spraying and the like. Furthermore, a scaffolding tubular structure may be strengthened by applying one or more rings of biocompatible polymer, such as Dacron to prevent tearing or crimping of the tubular graft ends. Alternatively, any materials including those identified above may be coated with the biocoacervate of the present invention utilizing the same process as described in the previous few sentences.

In view of such scaffolding structures, vessels and tubular grafts may be synthesized utilizing the biocoacervate and/or biomaterial. Generally, a vessel is a tubular graft made of the coacervates or biomaterials that can support the growth of cells on and/or within the coacervate or biomaterial. For example, vessels may be produced utilizing the coacervates or biomaterials that have the affinity to support growth of endothelial cells on the inside of the tube and smooth muscle cells on the outside of the tube. Furthermore, tubular grafts including such biocoacervates and biomaterials tend to have beneficial hemocompatible characteristics. Alternatively, a multi-layered vessel may be created with two or more separate tubes, wherein a smaller tube with endothelial cells grown on the inside of the tube is inserted into a larger tube with smooth muscle cells grown on the outside of the tube. Additional tubular layers may be included in the vessel that may or may not include the growth of cells on the surfaces or within the coacervates or biomaterials. The layers may also contain pharmacologically active agents and/or more structural components, such as polymeric materials, knitted materials or stents. The layers will generally stay in position through adhesives, fasteners like sutures, melted biocoacervate solvent welding, cell interaction, pressure fitting, cross-linking, intermolecular forces and other layer alignment means and may adhere or may not adhere to each other. It is also noted that layers that include cell growth may also include pharmacologically active agents.

Once prepared the tubular graft or vessel may be administered to the patient as a replacement to a damaged vessel or as a scaffolding device that can be inserted into or mounted around the damaged vessel. Vascular tubes, known as a STUNT (Support Tube Using New Technology) can be used for placement within a blood vessel. Embodiments of the tubular grafts have form memory and will reform if cut or severed back to its original form and shape. A vessel structure of the present invention will meet the mechanical and histological requirements of a blood vessel, while providing the biological and biochemical functions that are necessary for its success. One embodiment that ensures mechanical integrity and biological compatibility is a scaffold comprising collagen, elastin and heparin. These proteins are the primary components of a typical arterial wall. This will create the natural environment for the endothelial cells, while providing the structural characteristics of these proteins. Endothelialization of the cylindrical matrices will provide the critical hemocompatibility, while also providing the thrombolytic characteristics. This feature will allow for the creation of small-diameter vascular grafts with a reduction in thrombosis. Embodiments of the tubular structure will have a diameter of approximately 2-4 mm due to the small-diameters of native coronary arteries. However, the tubular structure could be any size. Due to the prevalence of coronary disease and the need for effective treatments, the proposed tubular structure would be embraced as a compatible vascular graft.

Additionally, since the vessels or tubular grafts of the present invention are produced with a biocompatible protein and may include the growth of cells from the patient or compatible cells, the vessel or tubular graft administered to the host tissue further enhances acceptance and remodeling of the vessel or tubular graft by the host tissue. It is again noted that a benefit of the coacervates or biomaterials of the present invention is the modifying, adapting and/or transforming of the device into an interwoven and/or functioning part of the host tissue.

Furthermore, the vessels and/or tubular grafts may also include one or more pharmacologically active agents within or attached to the coacervates or biomaterials that may assist in the facilitation of tissue acceptance and remodeling, as well as inhibit additional adverse conditions sometimes related to implantation of vessels, such as platelet aggregation, cell proliferation and/or angiogenesis activity, all of which may cause blockage of the vessel. In addition to antiplatelet aggregation drugs, anti-inflammatory agent, gene altering agents, angiogenesis inhibitors, antiproliferative agents, enzymes, growth factors and other additional pharmacologically active agents can be included in the vessel and/or tubular graft for localized administration to or near the host tissue.

Figure 5:
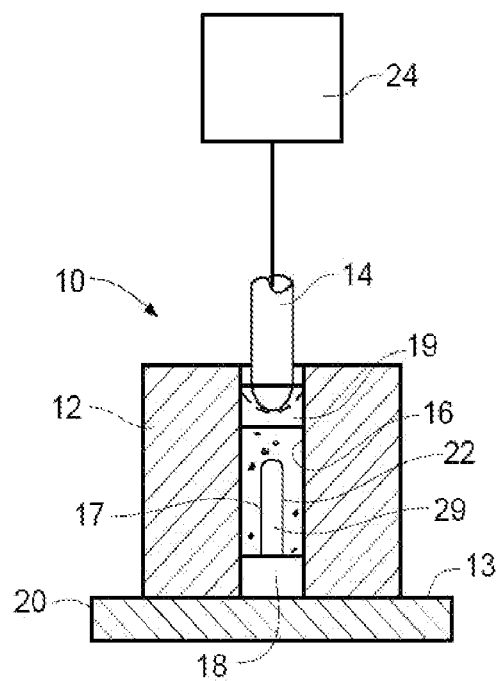
FIG. 5 depicts an embodiment of a compression molding device wherein the inner insert includes a mandrel.
Figure 6:
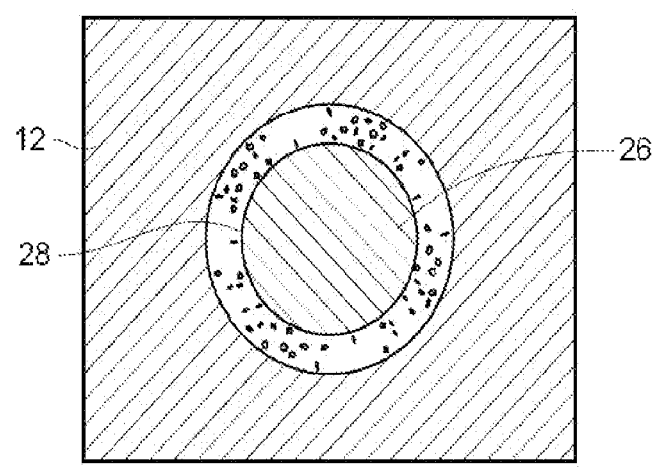
FIG. 6 depicts the top view of an embodiment of the compression molding device without the upper insert or plunger.

Embodiments of the biocoacervate or biomaterial vessels and/or tubular grafts may be prepared by methods similar to those described and suggested above. FIGS. 5 and 6 depict a compression molding device wherein the inner insert 18 includes a mandrel 29 that extends upward from the insert 18 into the chamber 17. FIG. 6 depicts a top view of the compression molding device without the upper insert 19 or plunger 14. Following the insertion of a sufficient amount of melted coacervate 22 the upper insert 19 and plunger 14 are applied to the coacervate 22. Once cooled, the vessel and/or tubular graft is then removed from the compression molding device and the vessel or graft is set utilizing a crosslinking technique. The vessel and/or tubular graft generally has a wall thickness of approximately 0.05 mm to 1 cm and preferably has a wall thickness of 0.15 to 1.5 mm.

Finally, the vessels may be set by utilizing one or more crosslinking techniques as disclosed or suggested above. It is noted, that the above mentioned vessels may optionally include one or more pharmacologically active agents or other structural additives, such as metal, insoluble proteins, polymeric and/or biocompatible materials including wire, ceramic, nylon, cotton or polymeric meshes or foams, especially foam, polymer, cotton or fiber tubes.

B. Fasteners (Sutures, Threads, Wraps . . . ):

As previously mentioned, other components that may be utilized with the vessel graft systems of the present invention include fasteners or drug delivery devices that include the coacervates or biomaterials of the present invention, such as sutures, threads, staples, meshes, wraps and the like. The fasteners/drug delivery devices may be configured in any shape and size to accommodate the securing or delivery of drug in the vessel graft systems.

Embodiments of the sutures, threads or wraps, also provide a fastener/device wherein pharmacologically active agents, such as those listed above, can be included within or attached to the surface. For example, the coacervates or biomaterials may include antiproliferative agents, such as paclitaxel or rapamycin, substances that help clotting, such as clotting factors, substances which are helpful for wound healing, such as vitamin E, as well as, anti-bacterial or anti-fungal agents to reduce the chance of infection. Other groups of pharmacologically active agents that may be delivered by the coacervates or biomaterials are analgesics, local anesthetics, other therapeutics to reduce pain, reduce scarring, reduce edema, and/or other type of drugs that would have very specific effects in the periphery and facilitate healing. Furthermore, the protein coacervate or biomaterial interacts with the cells that migrate to the wound to facilitate the healing process and that require a scaffolding before they can actually start working to close and remodel the wound area.

It is also possible to extend delivery of chemicals or drugs using the coacervate or biomaterial of the present invention in a layered suture, thread or wrap. In one embodiment this can be accomplished by providing suture, thread or wrap that includes a delivery system (e.g. a PEVA coating) positioned immediately behind a layer of the coacervate or biomaterial. In this example a suture, thread or wrap that includes a dosage of the chemical or pharmaceutical active component may be applied behind the coacervate or biomaterial, but not in immediate contact native tissue. By administering such a suture, thread or wrap, the delivery of chemicals and/or pharmaceuticals could be extended until the vessel has healed or the desired amount of chemicals and/or pharmaceuticals were applied. In application, the layer of coacervate or biomaterial would continue to absorb and deliver more chemicals and/or pharmaceuticals from the layer positioned below as the initial drug or chemical, if any, impregnated in the coacervate or biomaterial was being utilized in the adjacent tissue. Therefore, the coacervate or biomaterial would provide a controlled release of the chemical and/or pharmaceutical component and would prevent the administration of too much chemical and/or pharmaceutical component from entering a patient's tissue prematurely. Additionally, the coacervate or biomaterial with adjoining underlayer may be very beneficial for patients who are compromised in some way from internally supplying the biological substances needed to reduce or prevent them from healing quickly. Examples of such situations where such a coacervate or biomaterial wound healing device would be beneficial are in cases of diabetes, hemophilia, other clotting problems or any other type affliction that inhibits the adequate healing of a wound.

One method of preparing the biocompatible biological fasteners, such as sutures or threads, is to manufacture sheets of coacervate or biomaterial. Once the sheets of coacervate or biomaterial are prepared, each sheet may be cut into strips, threads or other shapes to form sutures, threads and other biological fasteners (e.g., hemostats). The sheets may be cut using cutting techniques known in the art. Also, the coacervate or biomaterial sutures or threads may be woven into sheets and used as a strengthened biomaterial weave that has desired porosity and can be used as a drug delivery wrap or fastener.

Additionally, fibers (large or small, e.g., macro, micro, nano) of a known suturing material (e.g. nylon, cotton . . . ) may be incorporated in, coated with or encapsulated in the coacervate or biomaterial when making a sheet of the biomaterial. Alternatively, a sheet of biocoacervate or biomaterial may be prepared, which includes known suture material. Once the sheet is prepared it may be cut by methods common to the art to produce a thread/suture that has biocompatible and durable characteristics.

Another method of preparing the biocompatible biological fasteners, such as sutures, threads, wraps, staples . . . , is to coat or encapsulate suturing threads (e.g. nylon, cotton . . . ) with the coacervate or biomaterial as described above. These fasteners can be coated or encapsulated by using any means known in the art (e.g. spray coating, dip coating, painting . . . ). Also, in various embodiments the suture, thread or wrap material may be loaded with one or more pharmacologically active agents prior to coating for delivery of such agents upon administration to the patient. For example, a cotton thread or suture may be loaded with one or more pharmacologically active agents by placing the thread or suture in a solvent including dissolved or suspended agent(s) to allow the agent(s) to absorb into the material of the suture or thread, thereby loading the thread or suture. Once loaded, the thread or suture may be coated or encapsulated with the biocoacervate and processed further for use in the vessel graft systems.

C. Bioglues and Adhesives:

The bioglues or adhesives that may be used with embodiments of the vessel graft system of the present invention can be can be used to adhere the native vessel and/or the surrounding host tissue to the vessel or tube of the vessel graft system. In general the bioglues or adhesives may be a biocoacervate adhesive of the present invention. In various embodiments of the present invention, a melted form of the biocoacervate can be administered to the vessel and/or the thread or suture wrapped or sutured at one or more ends of the vessel and/or host tissue. The melted biocoacervate is usually administered to the host tissue simultaneously or within a relatively short period of time (e.g. within 10 minutes) with a crosslinker (e.g. gluteraldehyde). Such administration of the liquid biocoacervate with the crosslinker causes a solidification of these components, thereby adhering and sealing the vessel and/or thread into position with the host tissue. The biocoacervate adhesive may be used to adhere host tissue to host tissue or host tissue to graft material. For example, the biocoacervate adhesive may be used to adhere a blood vessel graft to the native vessel by applying the adhesive to the native vessel and graft at the anastamosis site. This can assist in reducing blood seepage/leaking at the connection points of the graft and vessel including leaking at suture and other fastener points or related tears. Additionally, a cross-linker passivator (e.g. free-form protein, free-form peptide, polylysine, lysine, glutamine or glycine) can be included in the thread/suture or vessel as an additive or can be administered slightly before, simultaneously or shortly after administration of the cross-linker to the host tissue. The inclusion in the suture/thread and/or vessel or administration of such a passivator would deactivate any unused ends of the cross-linker that is present following interaction with the biocoacervate. It is noted, that the biocoacervate adhesive may also be used to produce a coating on surfaces of materials used to make the vessels and/or the threads/sutures to prepare the biocoacervate or biomaterial coating of such materials.

EXAMPLES

The biomaterial and biocoacervate vessel graft systems of the present invention and its components will now be further described with reference to the following non-limiting examples and the following materials and methods that were employed. Also, see Attachment A and the Attachment A Figures for other examples of the vessel graft system of the present invention and a study performed using the systems of the present invention and the materials used in such systems.

Example 1

Preparation of Biocoacervate

Soluble bovine collagen (Kensey-Nash Corporation) (1.5 gs) was dissolved in distilled water (100 mls) at 42° C. To this solution was added elastin (bovine neck ligament, 0.40 g) and sodium heparinate (0.20 g) dissolved in distilled water (40 mls) at room temperature. The elastin/heparin solution was added quickly to the collagen solution with minimal stirring thereby immediately producing an amorphous coacervate precipitate. The resulting cloudy mixture was let standing at room temperature for 1-2 hrs and then refrigerated. The rubbery precipitate on the bottom of the reaction flask was rinsed three times with fresh distilled water and removed and patted dry with filter paper to yield 6.48 gs of crude coacervate (MasterGel™) which was then melted at 55° C. and gently mixed to yield a uniform, rubbery, water-insoluble final product after cooling to room temperature. The supernatant of the reaction mixture was later dried down to a solid which weighed 0.417 g and was water soluble. The uniform MasterGel™ material was used to fabricate biocompatible structures for vessels, sutures and bioglues for the vessel graft systems.

Example 2

Biocoacervate Materials Including Additives and pH Solutions

MasterGel™ material was prepared as described in Example 1. Nine 1 g samples of MasterGel™ were cut and placed in a glass scintillation vial. The vial was then placed in a water bath at 60° C. and melted. Once melted either an additive or pH solution was added to each sample of MasterGel™. The following additives were administered: polyethylene glycol, chondroitin sulfate, hydroxyapatite, glycerol, hyaluronic acid and a solution of NaOH. Each of the above mentioned additives were administered at an amount of 3.3 mg separately to four melted samples of MasterGel™ with a few drops of water to maintain MasterGel™ viscosity during mixing. Each of the above mentioned additives were also administered at an amount of 10 mg to another four melted samples of MasterGel™ with a few drops of water to maintain MasterGel™ viscosity. Finally, NaOH was added to the final melted MasterGel™ sample until the MasterGel™ tested neutral with pH indicator paper. The uniform MasterGel™ material including additives or pH solution were crosslinked with 0.1% gluteraldehyde for 2 hours.

Example 3

Preparation of a Vessel

A open-cell polyurethane foam tube was fabricated with an outside diameter of 6 mm and a wall thickness of 1 mm. It is noted that a polypropylene/polytetrafluoroethylene mesh tube or cotton knit tube may be used rather than the polyurethane foam tube. This tube was placed into a container with sufficient coacervate (MasterGel) in the melted state to completely cover the tube. This combination was placed into a vacuum oven held at 55° C. and a vacuum pulled until trapped air in the polyurethane tube was removed. The vacuum was released and the MasterGel impregnated tube was cooled to room temperature and placed into distilled water followed by immersion in a 0.1% aqueous solution of glutaraldehyde for 2 hours. The resulting tubular graft was then suitable for use as a replacement vessel graft after appropriate sterilization.

Case Study:

Drug-Eluting Elastin-Collagen-Heparin Matrix (ECM Material) for Anastomosis Site Repair in Porcine Arterial Graft Studies Abstract:

Section: Targeted/Cellular Drug Delivery and Therapeutics (Biotec)

Purpose: Evaluation of non-clotting, non-throbogenic, regenerative coating material for long-term delivery of anti-proliferative drugs, rapamycin and paclitaxel, to inhibit smooth muscle cell hyperplasia (SMCH) after vascular repair. Methods: Drug-eluting threads (DETs) using 5 cm cotton thread (30/2), were evenly coated with 2 mg of drug into cotton or ethyl vinyl acetate (EVA) (3.5% EVA in xylene; FIG. 7). DETs were dip-coated in molten ECM material (MasterGel™), air-dried, crosslinked in glutaraldehyde (VasoCover™). DET elution studies were accomplished in sterile PBS (37° C.) using 7-day interval spectrophotometric analysis against standard curves (lower detection 5 ug/ml). In vivo work was performed in young adult porcine femoral artery graft studies.

Results: Paclitaxel-DET release fell precipitously after first week. Halfing rapamycin or paclitaxel dose in EVA topcoat and cotton increased initial drug release. Thinning VasoCover overcoat did not seem to have a significant effect on drug elution. Addition of half drug dose to EVA topcoat, results in greater release during the first two weeks, which falls off to a steady state thereafter. The thread with the thinnest EVA coat had the highest elution rate, while the thickest coat had the lowest (FIG. 14). Importantly, removal of EVA layer altogether ('rap$^3$') significantly boosts the elution of rapamycin, particularly from the third week on, but with a slight delay during week 1 compared to 'rap$^2$' (EVA-Drug mix) and 'rap$^4$' (thinned VasoCover). This is reflected in the total elution, as well, compared to all other rapamycin-DETs. Removal of EVA layer altogether favors a linear release profile, providing desired drug release characteristics with just ECM-VasoCover coating. In vivo porcine studies show that these perivascular DETs reduce and eliminate SMCH in small diameter blood vessel graft studies. Conclusion: The elution profile of rapamycin and paclitaxel was demonstrated from VasoCover coating of cotton with and without EVA polymer. Elution kinetics from VasoCover material alone provides desired time frame for clinical application to prevent stenosis from SMCH. We find VasoCover material provides drug elution for over 50 days in porcine femoral artery studies to inhibit SMCH, resulting in open <4 mm artificial femoral grafts lasting >6 months in ongoing studies.

Background:

Despite vast improvements in the field of biomaterials, an effective hemocompatible material is still not available for the production of vascular grafts, especially less than 5 mm, largely because of thrombosis, hyperplasia and clotting that leads to graft stenosis. Thus, vascular medical care can be dramatically enhanced by development of bio-artificial arteries. Gel-Del® Technologies tested its non-clotting and non-thrombogenic small vascular graft designed to overcome the eventual stenosis seen with currently available grafts (e.g. ePTFE, Dacron). The Gel-Del proprietary fabrication process uses purified proteins, carbohydrates, salts and water to produce biomimetic materials, including a tubular composite of type I collagen, elastin, salt, heparin and water that simulates the wall structure of blood vessels (VasoGraft™). This biomaterial, MasterGel™, is also a therapeutic delivery system to allow biochemical and pharmacological intervention of graft failure and facilitate host remodeling (rapamycin, AKA, Sirolimus™, is used to prevent anastomotic intimal hyperplasia). VasoGraft shows great promise in our 50 porcine subjects to benefit all blood vessel applications, including peripheral, coronary and carotid arteries. Our in vitro results demonstrate mechanical strength>2500 mmHg, heparin incorporation that prevents clotting/thrombogenicity, compliance, fluid transport, suture strength, suture reapproximation, semipermeability, and regenerative capacity complete with endothelial cell microvasculature and smooth muscle cell integration. Our NIH, SBIR phase I-II results from 30, 60, 90, 120 and 180-day in vivo tests in the porcine femoral artery model demonstrate excellent hemocompatibility, patency, and ingrowth of surrounding tissue (e.g., capillaries, fibroblasts, smooth muscle cells) into the graft material with no intimal hyperplasia of the graft itself. Implanted MasterGel material has been used to correct facial skin defects in a 150 subject successful FDA clinical trial, 2006-8.

We have been able to preclude or reduce the anastomotic intimal hyperplasia using the VasoGraft System to time-deliver rapamycin or paclitaxel, inhibitors of smooth muscle cell proliferation. The Gel-Del material is an excellent drug release vehicle and is shown to provide an effective mechanism to inhibit anastomotic intimal hyperplasia in studies lasting over 6 months. Incorporation of anti-proliferative drugs as a component of the graft system provides an answer for a common problem that plagues most vascular surgery interventions.

Objective:

In this study, we developed and tested drug eluting threads (DETs) to deliver anti-proliferative drugs, rapamycin (Sirolimus) and paclitaxel, to the anastomosis site of our artificial graft, VasoGraft™, and the porcine femoral artery, in vivo. DETs provide targeted and slow release of drug over months to preclude smooth muscle cell hyperplasia, allowing the native artery to heal without clogging itself (i.e., stenosis) so that the artery and graft stay patent (FIG. 9).

Materials & Methods:

In vitro DET release (FIG. 14) was measured spectrophotometrically (277 nm rapamycin, 227 nm paclitaxel). Assessment of DETs to inhibit smooth muscle cell hyperplasia in porcine femoral arteries grafted to VasoGraft was accomplished at VA Med. Ctr., Minneapolis, Minn. Standard surgical techniques were used (FIG. 9-10) with only post-op aspirin (imaging FIG. 17-18). Surface blood contact and platelet studies (FIG. 8,12) were accomplished by Medical Laboratory Surgical Services, Inc., St. Paul, Minn. Mechanical strength and perfusion studies (FIG. 13) by Tissue Growth Technologies, Minnetonka, Minn. In vitro, endothelial cell attachment to VasoGraft was accomplished with human umbilical vein endothelial cells (HUVEC cell line) pipeted into VasoGraft and incubated 4 days (FIG. 11). In vitro cell effects tested for rapamycin standard curve doses (FIG. 15).

Results:

DETs coated only with MasterGel/VasoCover provides the best release kinetics for rapamycin (rap3) when compared to EVA/MasterGel coatings (i.e., more linear and more drug eluted). EVA top coated with MasterGel/VasoCover provided predictable release kinetics, in vitro (FIG. 14).

CONCLUSIONS

Figure 17:
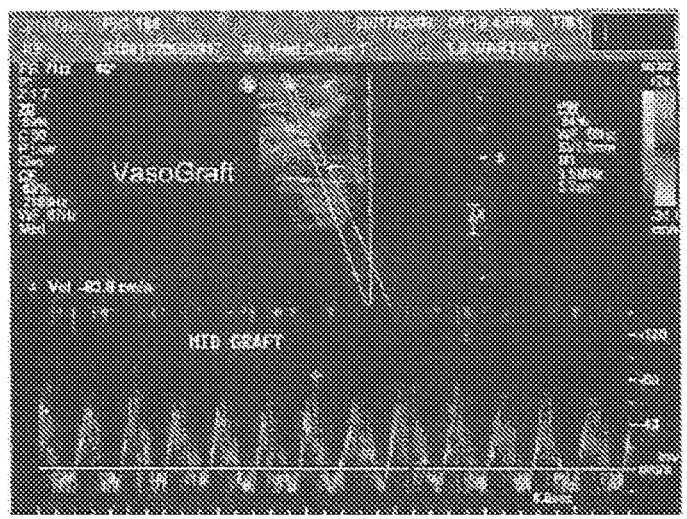
Figure 18:
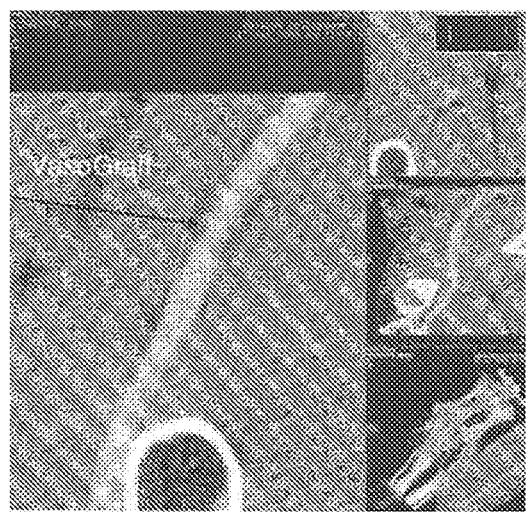
Figure 19:
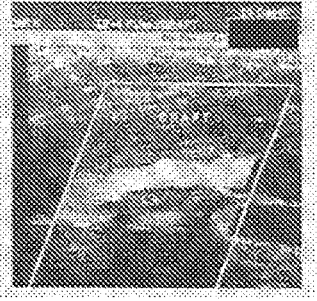

1. DET-rapamycin application prolongs or precludes smooth muscle cell hyperplasia in small diameter grafts, depending on proper delivery of drug dose at the anastomosis site (FIG. 16-19).
2. Thinning VasoCover does not affect drug release kinetics but significant differences are seen by removal of the EVA layer or by pre-loading half the drug in alternative EVA coat (FIG. 14).
3. VasoGraft™ small diameter artificial blood vessel graft stays fully patent for over 200 days with DET-rap applied to anastomosis site, without signs of rupture or fatigue (FIG. 17-19).

Additional Applications:

1. MasterGlue™, is MasterGel used as a sealant, tissue filler, and drug-elution vehicle to facilitate healing at anastomosis sites for injured or diseased vessels (FIG. 21-22).
2. MasterGel can be used to coat current vascular grafts or STENTS made from a variety of materials (e.g., ePTFE, poly urethane, cotton, steel, nitinol) at any coating thickness (FIG. 23-26).
3. MasterGel that is processed into VasoCover withstands high pressure (FIG. 24) and strongly attaches to STENTS with coatings that can be applied to submicron thickness (FIG. 25-26).
4. MasterGlue, VasoCover, and VasoGraft are made from MasterGel using GMP-ready scalable manufacturing that has already demonstrated long shelf life (FIG. 20).
5. ECM-MasterGel/VasoCover material converted to particles was shown safe and effective in an FDA-approved 150 subject clinical trial as an injected dermal repair implant (CosmetaLife™).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

The invention claimed is:

1. A vessel graft system comprising:
one or more tube(s) including one or more components, at least one of the components including a first biomaterial formed from one or more precipitated amorphous thermoplastic biocoacervate(s), the biocoacervate(s) including one or more soluble or solubilized primary proteins combined with one or more glycosaminoglycans and one or more biocompatible solvents and formed into a tubular configuration;
one or more threads, sutures and/or wraps positioned at one or more end(s) of one or more of the tube(s); the threads, sutures and/or wraps comprising one or more pharmacologically active agents and a biomaterial formed from a one or more precipitated amorphous thermoplastic biocoacervate(s), the biocoacervate(s) including one or more soluble or solubilized primary proteins combined with one or more glycosaminoglycans and one or more biocompatible solvents, wherein the threads, sutures and/or wraps deliver the one or more pharmacologically active agents to an anastomosis site; and,
a bioglue comprising a precipitated amorphous thermoplastic biocoacervate and one or more crosslinkers, the precipitated amorphous thermoplastic biocoacervate and one or more crosslinkers administered at the anastomosis site wherein the bioglue seals the threads, sutures and/or wraps at the anastomosis site.

2. The vessel graft system of claim 1 wherein the biocoacervates of the tube(s) and/or thread(s) are the same material.

3. The vessel graft system of claim 1 wherein the tube includes a structural scaffolding coated or encapsulated with the thermoplastic biomaterial.

4. The vessel graft system of claim 1 wherein the one or more primary proteins are selected from the group consisting of collagen, laminin, bone morphogenic protein and its isoforms that contain glycosaminoglycan binding sites, albumin, interleukins, epidermal growth factors, fibronectin, thrombin, aprotinin and antithrombin III.

5. The vessel graft system of claim 1 wherein the one or more glycosaminoglycans are selected from the group consisting of heparin, heparin sulfate, keratan sulfate, dermatin, dermatin sulfate, heparin-hyaluronic acid, chondroitin, chondroitin sulfate, chondroitin 6-sulfate, chondroitin 4-sulfate, chitin, chitosan, acetyl-glucosamine, hyaluronic acid, aggrecan, decorin, biglycan, fibromodulin, lumican and complexs thereof.

6. The vessel graft system of claim 1 wherein the tube further includes one or more secondary proteins.

7. The vessel graft system of claim 6 wherein the one or more secondary proteins are selected from the group consisting of fibrin, fibrinogen, elastin, albumin, ovalbumin, keratin, silk, silk fibroin, actin, myosin, thrombin, aprotinin and antithrombin III.

8. The vessel graft system of claim 1 wherein the one or more biocompatible solvents are selected from the group consisting of water, dimethyl sulfoxide (DMSO), biocompatible alcohols, biocompatible acids, oils and biocompatible glycols.

9. The vessel graft system of claim 1 wherein the one or more pharmacologically active agents are selected from the group consisting of analgesics, anesthetics, antiproliferative agents, angiogenesis inhibitors, angiogenic growth factors, steroids, antisteroids, corticosteroids, antiglacoma agents, antialcohol agents, anti-coagulant agents, genetic material, antithrombolytic agents, anticancer agents, anti-inflammatory agents, anticonception agents, enzymes agents, cells, growth factors, antiviral agents, antibacterial agents, antifungal agents and chemoattractants.

10. The vessel graft system of claim 9 wherein the one or more pharmacologically active agents are selected from the group consisting of paclitaxol, sirolimus, estradiol, dexamethazone, vitamin E, vitamin C, stem cells, superoxide dismutase, VEGF, FGF, EGF and cortizone.

11. The vessel graft system of claim 1 wherein the tube further includes one or more biocompatible additives.

12. The vessel graft system of claim 11 wherein the one or more biocompatible additives are selected from the group consisting of epoxies, polyesters, acrylics, nylons, silicones, polyanhydride, polyurethane, polycarbonate, poly(tetrafluoroethylene), polycaprolactone, polyalkenes, polyacrylates, bioceramic materials, polyethylene oxide, polyethylene glycol, poly(vinyl chloride), polylactic acid, polyglycolic acid, polypropylene oxide, poly(alkylene)glycol, polyoxyethylene, sebacic acid, polyvinyl alcohol, 2-hydroxyethyl methacrylate, polymethyl methacrylate, 1,3-bis(carboxyphenoxy)propane, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), glycosaminoglycans, bioceramic materials, insoluble proteins, proteins, amino acids, oils, fatty acids, salts, sugars, polypeptides, peptides, humectants, fibrin, graphite, flexible fluoropolymer, isobutyl-based, isopropyl styrene, vinyl pyrrolidone, cellulose acetate dibutyrate, silicone rubber, and copolymers of these.

13. The vessel graft system of claim 1 wherein the thermoplastic biomaterial is crosslinked with one or more crosslinking agents to form a crosslinked material.

14. The vessel graft system of claim 13 wherein the one or more cros slinking agents are selected from the group consisting of glutaraldehyde, 1,4-butandiol diglycidylether, formaldehyde, glyoxal, sebacic acid bis(N-succinimidyl) ester (DSS), p-Azidobenzolyl Hydazide, N-5-Azido 2-nitrobenzoyloxysuccinimide, N-Succinimidyl 6-[4' azido-2' nitro-phenylamino]hexanoate and 4-[p-Azidosalicylamido] butylamine.

15. The vessel graft system of claim 1 wherein the biomaterial included in the tube(s) and/or the thread(s) comprises collagen, heparin, elastin and water.

16. A vessel graft system comprising:
one or more tube(s) including one or more components, at least one of the components including a first biomaterial formed from one or more precipitated amorphous thermoplastic biocoacervate(s), the biocoacervate(s) including one or more soluble or solubilized primary proteins combined with one or more glycosaminoglycans and one or more biocompatible solvents and formed into a tubular configuration;
one or more threads, sutures and/or wraps positioned at one or more end(s) of one or more of the tube(s); the threads, sutures and/or wraps comprising one or more components, wherein at least one of the component(s) including a biomaterial formed from a one or more precipitated amorphous thermoplastic biocoacervate(s), the biocoacervate(s) including one or more soluble or solubilized primary proteins combined with one or more glycosaminoglycans and one or more biocompatible solvents; and
a bioglue comprising a precipitated amorphous thermoplastic biocoacervate and one or more crosslinkers, wherein the bioglue seals the threads, sutures and/or wraps at an anastomosis site.

17. The vessel graft system of claim 16, wherein one or more threads, sutures and/or wraps further comprises one or more pharmacologically active agents and wherein the threads, sutures and/or wraps delivery the one or more pharmacologically active agents to the anastomosis site.

* * * * *

SEQUENCE LISTING

<160> NUMBER OF SEQ ID NOS: 21

<210> SEQ ID NO 1
<211> LENGTH: 59
<212> TYPE: PRT
<213> ORGANISM: Artificial
<220> FEATURE:
<223> OTHER INFORMATION: synthetic construct similar to silk protein.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ser Gly Ala Gly Ala Gly Ser Gly Ala
            20                  25                  30

Gly Ala Gly Ser Gly Ala Gly Ala Gly Ser Gly Ala Gly Ser
        35                  40                  45

Gly Ala Gly Ala Gly Ser Gly Ala Ala Gly Tyr
    50                  55

<210> SEQ ID NO 2
<211> LENGTH: 6
<212> TYPE: PRT
<213> ORGANISM: Artificial
<220> FEATURE:
<223> OTHER INFORMATION: synthetic construct similar to silk protein.

<400> SEQUENCE: 2

Gly Ala Gly Ala Gly Ser
1               5

<210> SEQ ID NO 3
<211> LENGTH: 71
<212> TYPE: PRT
<213> ORGANISM: Artificial
<220> FEATURE:
<223> OTHER INFORMATION: synthetic construct similar to silk protein.

<400> SEQUENCE: 3

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Gly Arg Gly Asp Ser
    50                  55                  60

Pro Ala Ser Ala Ala Gly Tyr
65                  70

<210> SEQ ID NO 4
<211> LENGTH: 74
<212> TYPE: PRT
<213> ORGANISM: Artificial
<220> FEATURE:
<223> OTHER INFORMATION: synthetic construct similar to silk protein.

<400> SEQUENCE: 4

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Ala Gly Pro Ser Ala Gly Tyr
65                  70

<210> SEQ ID NO 5
<211> LENGTH: 73
<212> TYPE: PRT
<213> ORGANISM: Artificial
<220> FEATURE:
<223> OTHER INFORMATION: synthetic construct similar to silk protein.

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Ala Ala Pro Gly Ala Ser Ile Lys Val
        50                  55                  60

Ala Val Ser Gly Pro Ser Ala Gly Tyr
65                  70

<210> SEQ ID NO 6
<211> LENGTH: 71
<212> TYPE: PRT
<213> ORGANISM: Artificial
<220> FEATURE:
<223> OTHER INFORMATION: synthetic construct similar to silk protein.

<400> SEQUENCE: 6

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Arg Tyr Val Val Leu Pro Arg Pro Val Cys
        50                  55                  60

Phe Glu Lys Ala Ala Gly Tyr
65                  70

<210> SEQ ID NO 7
<211> LENGTH: 20
<212> TYPE: PRT
<213> ORGANISM: Artificial
<220> FEATURE:
<223> OTHER INFORMATION: synthetic construct similar to elastin protein.

<400> SEQUENCE: 7

Val Pro Gly Val Gly Val Pro Gly Val Gly Pro Gly Val Gly Val
1               5                   10                  15

Pro Gly Val Gly
            20

<210> SEQ ID NO 8
<211> LENGTH: 52
<212> TYPE: PRT
<213> ORGANISM: Artificial
<220> FEATURE:
<223> OTHER INFORMATION: synthetic construct similar to elastin protein.

<400> SEQUENCE: 8

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
            35                  40                  45

Gly Ala Gly Ser

-continued

<210> SEQ ID NO 9
<211> LENGTH: 82
<212> TYPE: PRT
<213> ORGANISM: Artificial
<220> FEATURE:
<223> OTHER INFORMATION: synthetic construct similar to elastin protein.

<400> SEQUENCE: 9

Gly Ala Ala Val Pro Gly Val Gly Val Pro Gly Val Gly Val Pro Gly
1               5                   10                  15

Val Gly Val Pro Gly Val Gly Val Ala Ala Gly Tyr Gly Ala Gly Ala
                20                  25                  30

Gly Ser Gly Ala Gly Ala Gly Ser Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser

<210> SEQ ID NO 10
<211> LENGTH: 111
<212> TYPE: PRT
<213> ORGANISM: Artificial
<220> FEATURE:
<223> OTHER INFORMATION: synthetic construct similar to elastin protein.

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Ala Gly Tyr Gly Ala Gly Ala Gly Ser Gly
            35                  40                  45

Ala Gly Ala Gly Ser Gly Ala Gly Ala Gly Ser Gly Ala Gly Ala Gly
        50                  55                  60

Ser Gly Ala Gly Ala Gly Ser Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro
            100                 105                 110

<210> SEQ ID NO 11
<211> LENGTH: 88
<212> TYPE: PRT
<213> ORGANISM: Artificial
<220> FEATURE:
<223> OTHER INFORMATION: synthetic construct similar to elastin protein.

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
            35                  40                  45

```
Gly Ala Gly Ser Gly Ala Gly Ala Gly Ser Gly Ala Gly Ser
            50                  55                  60

Gly Ala Gly Ala Gly Ser Gly Ala Gly Ala Gly Ser Gly Ala Gly Ala
 65                  70                  75                  80

Gly Ser Gly Ala Gly Ala Gly Ser
                85
```

```
<210> SEQ ID NO 12
<211> LENGTH: 108
<212> TYPE: PRT
<213> ORGANISM: Artificial
<220> FEATURE:
<223> OTHER INFORMATION: synthetic construct similar to elastin protein.

<400> SEQUENCE: 12

Gly Val Gly Val Pro Gly Val Gly Val Pro Gly Val Gly Val Pro Gly
  1               5                  10                  15

Val Gly Val Pro Gly Val Gly Val Pro Gly Val Gly Val Pro Gly Val
                 20                  25                  30

Gly Val Pro Gly Val Gly Val Pro Gly Val Gly Val Pro Gly Val Gly
             35                  40                  45

Val Pro Gly Val Gly Val Pro Gly Val Gly Val Pro Gly Ala Gly Ala
         50                  55                  60

Gly Ser Gly Ala Gly Ala Gly Ser Gly Ala Gly Ala Gly Ser Gly Ala
 65                  70                  75                  80

Gly Ala Gly Ser Gly Ala Gly Ala Gly Ser Gly Ala Gly Ala Gly Ser
                 85                  90                  95

Gly Ala Gly Ala Gly Ser Gly Ala Gly Ala Gly Ser
            100                 105
```

```
<210> SEQ ID NO 13
<211> LENGTH: 128
<212> TYPE: PRT
<213> ORGANISM: Artificial
<220> FEATURE:
<223> OTHER INFORMATION: synthetic construct similar to elastin protein.

<400> SEQUENCE: 13

Gly Val Gly Val Pro Gly Val Gly Val Pro Gly Val Gly Val Pro Gly
  1               5                  10                  15

Val Gly Val Pro Gly Val Gly Val Pro Gly Val Gly Val Pro Gly Val
                 20                  25                  30

Gly Val Pro Gly Val Gly Val Pro Gly Val Gly Val Pro Gly Val Gly
             35                  40                  45

Val Pro Gly Val Gly Val Pro Gly Val Gly Val Pro Gly Val Gly Val
         50                  55                  60

Pro Gly Val Gly Val Pro Gly Val Gly Val Pro Gly Val Gly Val Pro
 65                  70                  75                  80

Gly Ala Gly Ala Gly Ser Gly Ala Gly Ala Gly Ser Gly Ala Gly Ala
                 85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125
```

```
<210> SEQ ID NO 14
<211> LENGTH: 208
<212> TYPE: PRT
<213> ORGANISM: Artificial
```

<220> FEATURE:
<223> OTHER INFORMATION: synthetic construct similar to elastin protein.

<400> SEQUENCE: 14

```
Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
            35                  40                  45
Val Pro Gly Val Gly Val Pro Gly Val Gly Val Pro Gly Val Gly Val
        50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
                100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
        130                 135                 140
Pro Gly Val Gly Val Pro Gly Val Gly Val Pro Gly Val Gly Val Pro
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
                180                 185                 190
Gly Ala Gly Ser Gly Ala Gly Ala Gly Ser Gly Ala Gly Ala Gly Ser
            195                 200                 205
```

<210> SEQ ID NO 15
<211> LENGTH: 76
<212> TYPE: PRT
<213> ORGANISM: Artificial
<220> FEATURE:
<223> OTHER INFORMATION: synthetic construct similar to elastin protein.

<400> SEQUENCE: 15

```
Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Ala Gly Ala Gly Ser Gly Ala
            35                  40                  45
Gly Ala Gly Ser Gly Ala Gly Ala Gly Ser Gly Ala Gly Ala Gly Ser
        50                  55                  60
Gly Ala Gly Ala Gly Ser Gly Ala Gly Ala Gly Ser
65                  70                  75
```

<210> SEQ ID NO 16
<211> LENGTH: 64
<212> TYPE: PRT
<213> ORGANISM: Artificial
<220> FEATURE:
<223> OTHER INFORMATION: synthetic construct similar to elastin protein.

<400> SEQUENCE: 16

```
Gly Val Gly Val Pro Gly Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

<210> SEQ ID NO 17
<211> LENGTH: 56
<212> TYPE: PRT
<213> ORGANISM: Artificial
<220> FEATURE:
<223> OTHER INFORMATION: synthetic construct similar to keratin protein.

<400> SEQUENCE: 17

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55

<210> SEQ ID NO 18
<211> LENGTH: 15
<212> TYPE: PRT
<213> ORGANISM: Artificial
<220> FEATURE:
<223> OTHER INFORMATION: synthetic construct similar to collagen
      protein.

<400> SEQUENCE: 18

Gly Ala Pro Gly Pro Pro Gly Pro Pro Gly Pro Pro Gly Pro Pro
1               5                   10                  15

<210> SEQ ID NO 19
<211> LENGTH: 39
<212> TYPE: PRT
<213> ORGANISM: Artificial
<220> FEATURE:
<223> OTHER INFORMATION: synthetic construct similar to collagen
      protein.

<400> SEQUENCE: 19

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 20
<211> LENGTH: 63
<212> TYPE: PRT
<213> ORGANISM: Artificial
<220> FEATURE:
<223> OTHER INFORMATION: synthetic construct similar to collagen
      protein.

<400> SEQUENCE: 20
```

-continued

```
Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 21
<211> LENGTH: 15
<212> TYPE: PRT
<213> ORGANISM: Artificial
<220> FEATURE:
<223> OTHER INFORMATION: synthetic construct similar to collagen
      protein.

<400> SEQUENCE: 21

Gly Ala Pro Gly Ala Pro Gly Ser Gln Gly Ala Pro Gly Leu Gln
1               5                   10                  15
```